US010045729B2

(12) United States Patent
Suarez et al.

(10) Patent No.: US 10,045,729 B2
(45) Date of Patent: Aug. 14, 2018

(54) HEAD TILT RESPONSE

(75) Inventors: Hamlet Suarez, Montevideo (UY); Alejo Suarez, Montevideo (UY); Dario Geisinger, Montevideo (UY); Nicolas Fernandez Tournier, Montevideo (UY)

(73) Assignee: Laboratorio de Otoneurologia, Montevideo (UY)

( * ) Notice: Subject to any disclaimer, the term of this patent is extended or adjusted under 35 U.S.C. 154(b) by 1479 days.

(21) Appl. No.: 13/267,378

(22) Filed: Oct. 6, 2011

(65) Prior Publication Data

US 2012/0089049 A1 Apr. 12, 2012

Related U.S. Application Data

(60) Provisional application No. 61/390,563, filed on Oct. 6, 2010.

(51) Int. Cl.
| | |
|---|---|
| *A61B 5/00* | (2006.01) |
| *A61B 5/11* | (2006.01) |
| *G16H 50/20* | (2018.01) |
| *A61B 3/113* | (2006.01) |

(52) U.S. Cl.
CPC ............ *A61B 5/4023* (2013.01); *A61B 5/11* (2013.01); *A61B 5/6803* (2013.01); *A61B 5/6814* (2013.01); *A61B 5/7235* (2013.01); *G16H 50/20* (2018.01); *A61B 3/113* (2013.01)

(58) Field of Classification Search
CPC ......... A61B 3/113; A61B 5/11; A61B 5/6803; A61B 5/6814; A61B 5/7235; A61B 5/0496; A61B 5/4023; A61B 2562/0219; G02B 27/0093; G06F 19/345

USPC .......................................... 600/587, 594, 595
See application file for complete search history.

(56) References Cited

U.S. PATENT DOCUMENTS

| | | | | |
|---|---|---|---|---|
| 5,373,857 A | * | 12/1994 | Travers et al. ................ | 600/595 |
| 5,942,954 A | * | 8/1999 | Galiana ................. | A61B 3/113 |
| | | | | 351/209 |
| 8,016,770 B2 | * | 9/2011 | Chiba et al. ................... | 600/558 |
| 8,585,609 B2 | * | 11/2013 | Kiderman .............. | A61B 3/113 |
| | | | | 600/558 |
| 2004/0006287 A1 | * | 1/2004 | Epley ....................... | A61B 5/11 |
| | | | | 600/595 |
| 2004/0097839 A1 | * | 5/2004 | Epley ................... | A61B 5/0484 |
| | | | | 600/595 |
| 2005/0099601 A1 | * | 5/2005 | MacDougall et al. ......... | 351/209 |
| 2005/0216243 A1 | * | 9/2005 | Graham et al. .................. | 703/11 |
| 2007/0161875 A1 | * | 7/2007 | Epley ............................. | 600/301 |
| 2010/0016730 A1 | * | 1/2010 | Tanaka et al. ................. | 600/476 |

(Continued)

OTHER PUBLICATIONS

Böhmer, Andreas; Mast, Fred. Assessing Otolith Function by the Subjective Visual Vertical. Annals of the New York Academy of Sciences: 871,1999, pp. 221-231.

(Continued)

*Primary Examiner* — Adam J Eiseman
(74) *Attorney, Agent, or Firm* — Nixon Peabody LLP

(57) ABSTRACT

The present invention relates to the estimation of the vertical in humans using an experimental design that incorporates virtual reality. Methods of measuring the perceived vertical in a subject using steady state and transient experiments are disclosed. The inventive methods are useful for diagnosis, as well as for follow up after patient rehabilitation.

3 Claims, 21 Drawing Sheets

(56) References Cited

U.S. PATENT DOCUMENTS

2012/0218285 A1* 8/2012 Crane .................. G06T 11/00
                                                        345/589

OTHER PUBLICATIONS

Böhmer, Andreas. The Subjective Visual Vertical as a Clinical Parameter for Acute and Chronic Vestibular (Otolith) Disorders. ActaOtolaryngol (Stockh) 1999; 119; 126-127.

Bronstein AM. The interaction of otolith and proprioceptive information in the perception of verticality. The effects of labyrinthine and CNS disease. Ann. NY Acad. Sci. May 28, 1999; 871:324-33.

Clarke, A. H. And Engelhorn, A. Unilateral testing of utricularfunction. Exp. Brain Res. 121 (1998). 457-464.

Clarke, A. H. The many facets of the otolith—a review. J VestibRes 11(3-5), 314 (2002).

Daddaoua, Nabil. Dicke, Peter W. Their, Peter. The subjective visual vertical in a nonhuman primate. Journal of Vision (2008)8(3):19, 1-8.

Fischer, M. H. Z. Messende Untersuchungen über die Gegenrollungder Augen and die Lokalisation der scheinbaren Vertikalen. v. Graefe's Arch. Ophthal. 118 (1927). 633-680.

Kobayashia, Hironari. Hayashia, Yujiro. Higashinoa, Kazutaka. Saitob, Akira. Kunihiroa, Takanobu. Kanzakia, Jin and Goto, Fumiyuki. Dynamic and static subjective visual vertical with aging. Auris Nasus Larynx vol. 29, Issue 4, 1 Oct. 2002, pp. 325-328.

Mars, Franck; Vercher, Jean-Louis and Blouin, Jean. Perception of the vertical with a head-mounted visual frame during head tilt, Ergonomics (2004), 47:10, 1116-1130.

Nechel, Ch. Van, Toupet, M. Bodsona, I. The Subjective Visual Vertical. Otolith Functions and Disorders. Adv Otorhinolaryngol. Basel, Karger, 2001, vol. 58, pp. 77-87.

Schöne, H. Über den Einfluß der Schwerkraft auf die Augenrollungund die Wahrnehmung der Lage im Raum. Z. vergl. Physiol. 46 (1962), 57-87.

Wetzig, J. Hofstetter-Degen, K. Maurer, J. And Baumgarten, R. von. Clinical verification of a unilateral otolith test. Acta Astronautica 27 (1992). 19-24.

Wuyts, F. L. Hoppenbrouwers, M. Pauwels, G. and Heyning, P. vande. Unilateral otolith function testing—is the utricular function additive? Abstract Barany Meeting 2002. J Vestib. Res. 11 (2002). 304.

* cited by examiner a)  b)  c)

| PATIENTS | | | | | | | |
|---|---|---|---|---|---|---|---|
| Patient | Gender | Age | Diagnosis | CHRONIC DIZZINESS | Group | SSE | TRS |
| 1 | M | 25 | MD | + | A | -0.68 | 5.07 |
| 2 | F | 61 | PANS | + | A | -0.01 | 2.39 |
| 3 | F | 36 | MD | + | A | -0.55 | 2.40 |
| 4 | F | 24 | VN | + | A | -0.46 | 1.44 |
| 5 | F | 26 | CVSL | + | A | -0.47 | 2.33 |
| 6 | F | 46 | PANS | + | A | -0.11 | 2.87 |
| 7 | F | 21 | CVSL | + | A | -0.52 | 2.00 |
| 8 | M | 42 | MD | + | A | 0.14 | 5.19 |
| 9 | M | 59 | MD | - | B | 0.12 | 2.09 |
| 10 | M | 34 | MD | - | B | -0.06 | 1.69 |
| 11 | M | 31 | MD | - | B | -0.05 | 1.79 |
| 12 | F | 30 | MD | - | B | 0.01 | 1.21 |

HEAD TILT RESPONSE

CROSS-REFERENCE TO RELATED APPLICATIONS

This application claims priority from U.S. Provisional Patent Application No. 61/390,563, filed on Oct. 6, 2010, which is incorporated herein by reference in its entirety.

FIELD OF THE INVENTION

The invention generally relates to a method and device for measuring the perception of the gravitational vertical.

BACKGROUND

All publications herein are incorporated by reference to the same extent as if each individual publication or patent application was specifically and individually indicated to be incorporated by reference. The following description includes information that may be useful in understanding the present invention. It is not an admission that any of the information provided herein is prior art or relevant to the presently claimed invention, or that any publication specifically or implicitly referenced is prior art.

The perception of the gravitational vertical (GV) depends upon the integration of otolith, visual, proprioceptive and somatosensory information. The estimation of the vertical has important consequences in one's perception of the world, yet the fundamentals and mechanisms involved in this perception are still unclear. An inaccurate perception of the gravitational vertical has been associated with otolith dysfunction. Thus, effective modeling and testing of the perception of the gravitational vertical are needed.

SUMMARY OF THE INVENTION

In certain embodiments, the present invention teaches a method for determining a subject's perception of the gravitational vertical, the method including: providing a subject with eyewear capable of displaying an image; displaying an image on the eyewear at an angle to the gravitational vertical; measuring and recording the position and movement of the subject's head in response to the image using a processor; and determining the subject's perception of the gravitational vertical based on the measured and recorded position and movement. In some embodiments, the subject is isolated from visual stimuli, apart from the image. In some embodiments, successive images are displayed periodically, at angles from the gravitational vertical, and the subject's response to each image is measured and recorded. In certain embodiments, an electronic tracking device is used for the measuring and recording. In some embodiments eye movements in one or both eyes of the subject are also tracked. In some embodiments, the eye movements tracked are horizontal and/or vertical. In certain embodiments, the eye movements tracked are rotations performed by the eyes.

In some embodiments, the invention discloses a method for diagnosing otolith dysfunction, including: providing a subject with eyewear capable of displaying an image; displaying an image on the eyewear at an angle to the gravitational vertical; measuring and recording the position and movement of the subject's head in response to the image using a processor; and diagnosing the subject with otolith dysfunction if the subject has an abnormal response, or diagnosing the subject as having normal otolith function if the subject has a normal response.

In some embodiments the invention teaches a method for assessing a level of compensation for otolith dysfunction in a subject who has undergone rehabilitation, including: providing a subject who has undergone rehabilitation with eyewear capable of displaying an image; displaying an image on the eyewear at an angle to the gravitational vertical; measuring and recording the position and movement of the subject's head in response to the image using a processor; and assessing the level of compensation for otolith dysfunction in the subject, based upon the subject's response. In certain embodiments, the subject is isolated from visual stimuli, apart from the image. In some embodiments, successive images are displayed periodically, at angles from the gravitational vertical, and the subject's response to each image is measured and recorded. In certain embodiments, the movement and position of the subject's head are tracked and recorded with an electronic tracking device. In some embodiments, eye movements are tracked in one or both eyes of the subject. In some embodiments, the eye movements tracked are horizontal and/or vertical. In some embodiments, the eye movements tracked are rotations performed by the eyes.

In certain embodiments, the invention teaches a system for determining a subject's perception of the gravitational vertical, the system including: virtual reality goggles configured to display an image at an angle to the gravitational vertical; an electronic means for generating the image; an electronic means for measuring and recording the motion and position of the subject's head in response to the image; a data storage comprising a head motion and position capturing and analyzing application; and a processor operatively coupled to: the electronic means for measuring and recording the motion and position of the subject's head in response to the image, the virtual reality goggles, and the electronic means for generating the image, wherein, upon execution, the electronic means for generating the image generates the image, the virtual reality goggles display the image, and the electronic means for recording the motion and position of the subject's head in response to the image records the motion and position of the subject's head, and a subject's perception of the gravitational vertical is determined. In certain embodiments, the system further includes: a means for tracking the motion of a subject's eyes; and an eye motion tracking application, wherein the processor is operatively coupled to the means for tracking the motion of the subject's eyes, and wherein upon execution, the means for tracking the motion of the subject's eyes tracks the motion of the subject's eyes.

In certain embodiments, the invention teaches a computer readable medium having computer-executable components that, when executed by a computing device coupled to: virtual reality goggles capable of displaying an image, an electronic means for generating the image, and one or more electronic means for measuring and recording the motion and position of the subject's head and/or eyes in response to the image, cause: the virtual reality goggles to display an image at an angle to the gravitational vertical; the electronic means for measuring and recording the motion and position of the subject's head and/or eyes in response to the image to measure and record the motion and position of the subject's head and/or eyes in response to the image; and the computing device to determine parameters related to the subject's response to the image, based upon the measurements. In some embodiments, the parameters determined are selected from the group consisting of: steady state error (SSE), delay time (TDT), rise time (TRS), settling time (TST), overshoot (OSP), integral time square absolute error (IT2AE) and combinations thereof.

BRIEF DESCRIPTION OF THE DRAWINGS

FIG. 23 demonstrates, in accordance with an embodiment of the invention, information about the 12 patients studied. M=male, F=female, MD=Meniere Disease, PANS=Post Acoustic Neuroma Surgery, VN=Vestibular Neuronitis, CVSL=Cochleo-vestibular sudden loss. The sign (+) shows the PVH patients who had chronic dizziness and the sign (−) those who haven't this symptom. TRS=Rise time. SSE=Steady state error.

DESCRIPTION OF THE INVENTION

Figure 1:
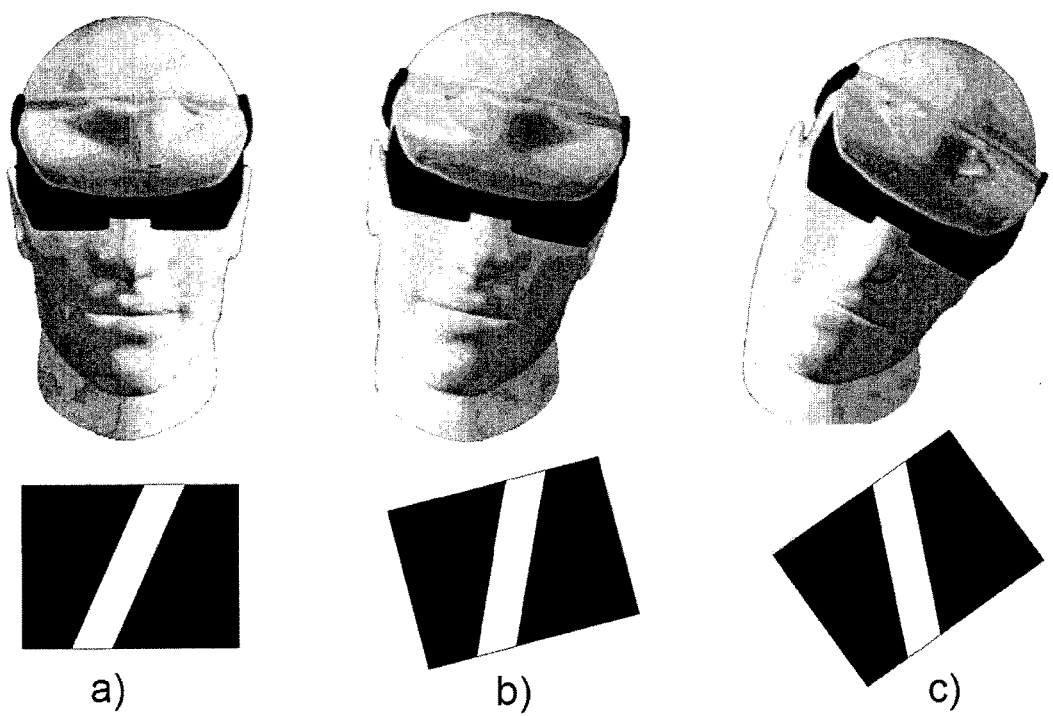
FIG. 1 demonstrates, in accordance with an embodiment of the invention: a) a subject with his head in an upright position and the image seen on the goggles represented as the white stripe over a black background; b) a subject with his head tilted (the white stripe is closer to the GV but has not yet reached it); and c) a subject with his head tilted, and the white stripe slightly over rotated. The GV would be matched with a head position between b) and c). Images are as seen by the subject.

All references cited herein are incorporated by reference in their entirety as though fully set forth. Unless defined otherwise, technical and scientific terms used herein have the same meaning as commonly understood by one of ordinary skill in the art to which this invention belongs.

One skilled in the art will recognize many methods and materials similar or equivalent to those described herein, which could be used in the practice of the present invention. Indeed, the present invention is in no way limited to the methods and materials described.

As used herein:

The acronym "GV" means gravitational vertical

The acronym "SVV" means subjective visual vertical

The acronym "HTR" means head tilt response

The acronym "dHTR" means dynamic response

The acronym "sHTR" means static response

The acronym "HMD" means head mounted display

The acronym "ENG" means electronystagmography

The acronym "UVL" means unilateral vestibular loss

The acronym "BVL" means bilateral vestibular loss

The acronym "SSE" means steady state error

The acronym "TDT" means delay time

The acronym "TRS" means rise time

The acronym "TST means settling time

The acronym "OSP" means overshoot

The acronym "IT2AE" means integral time square absolute error

The acronym "VEO" means vestibular end organs

Perception of the gravitational vertical (GV) can be tested in numerous ways, a few non-limiting examples include: earth vertical saccades in darkness, adjusting the body to the vertical or horizontal or Subjective Visual Vertical (SVV) [2].

The Subjective Visual Vertical (SVV) is a test that assesses the perception of the gravitational vertical. It consists of visualizing an illuminated rod or bar which can rotate in its midpoint along the horizontal axis by means of a controller. The test is done in a completely dark room, so the subject has no external visual cues besides the rod, which is initially set in a random position (random tilt angle). The objective is to align the bar or rod to the gravitational vertical by rotating it with the controller. No feedback other than the visual feedback should be present. From its original presentation [1], several variations of this experiment have been performed [10, 17], including variations that involve a dynamic background [12] and unilateral otolith stimulation [22, 6, 23]

The perception of the GV depends upon the integration of otolith, visual, proprioceptive and somatosensory information [3,8,4]. It has been further suggested that in the case of the SVV, the wrong perception of the GV implies otolith dysfunction [7, 18]. In the case of the SVV, the central nervous system must fuse information from various sources in order to determine that a lighted bar is aligned with the GV. Such information includes: retinal image, vestibular, proprioceptive, cutaneous, muscular and articular to determine the alignment of the head relative to the trunk [13,5,14] and appears to be roll-angle dependent [20].

The inventors explored the phenomenon of the perception of the GV through an experiment named Head Tilt Response (HTR). This experimentation involves a dynamic approach in which a subject actively adjusts his head position to match a visual stimulus to the GV. HTR can be viewed as complementary to the SVV, because the source of information that the brain receives in the SVV and HTR is the same, but the dynamics of that information are complementary.

The analysis of the data supposes the system is a multi-input (visual, vestibular and proprioceptive) and an output (inclination of the head related to the GV), regarding the processing as a "black box" control system.

The present invention is based, at least in part, on these findings as well as others further described herein.

In one embodiment, the present invention provides a method for determining a subject's perception of the gravitational vertical. The method includes: providing a subject with eyewear capable of displaying an image; displaying an image on the eyewear at an angle to the gravitational vertical; measuring and recording the position and movement of the subject's head in response to the image using a processor, and determining the subject's perception of the gravitational vertical based on the measured and recorded position and movement. In various embodiments, the subject is isolated from visual stimuli, apart from the image. In various embodiments, successive images are displayed periodically, at angles from the gravitational vertical, and the subject's response to each image is measured and recorded. In certain embodiments, the movement and position of the subject's head is measured and recorded with an electronic tracking device. In an embodiment the head tracking device is an InertiaCube2+, Intersense device. In certain embodiments, the image is a bar or a line. In certain embodiments, the image is of a type in which rotation can be perceived. In some embodiments, the eyewear is a pair of virtual reality goggles. In an embodiment, the virtual reality goggles are Z800 3Dvisor, eMargin. In certain embodiments, the interval between successive images is uniform. In other embodiments, the interval between successive images is not uniform. In some embodiments, the change in the angle to gravitational vertical between successive images is uniform. In other embodiments, the change in angle to the gravitational vertical between successive images is not uniform. In certain embodiments, the change in angle to the gravitational vertical between successive images in an examination varies such that transitions between positive and negative angles with respect to the gravitational vertical are tested. In certain embodiments, changes in the angle to the gravitational vertical between successive images are included such that transitions of head position between successive negative angles and/or positive angles to the gravitational vertical are tested. In certain embodiments, combinations of one or more responses to transitions between positive-positive, negative-negative, negative-positive and positive to negative angles of images to the gravitational vertical are tested. The angle of the image from gravitational vertical displayed during the test is any positive or negative angle that allows a patient to respond within the range of motion of his or her head.

In certain embodiments, the parameters evaluated in a subject's response are selected from the group consisting of: steady state error (SSE), delay time (TDT), rise time (TRS), settling time (TST), overshoot (OSP), integral time square absolute error (IT2AE) and combinations thereof. In an embodiment a larger than normal TRS observed in a patient is indicative of distorted vestibular end organ input. In some embodiments, a delay in reaching gravitational vertical, determined in a subject using one or more of the inventive methods, indicates a lack of full sensory substitution for vestibular loss. In an embodiment, an abnormal value of IT2AE alone, determined according to one or more testing methods disclosed herein, is indicative of a vestibular disorder. In another embodiment, evaluation of two or more parameters disclosed herein, ascertained according to the inventive methods disclosed herein, is used to diagnose a vestibular disorder. In certain embodiments, evaluation of SSE and TRS parameters is used to characterize the transient response of a subject to one or more experiments disclosed in the inventive methods herein. In certain embodiments, an abnormal transient response, determined by evaluating said parameters compared to those of a normal subject, is indicative of a vestibular and/or balance disorder.

In certain embodiments, the subject performs the test while sitting. In some embodiments, the subject, whether standing or sitting, is not in an upright position. The subject can be positioned on an inclined surface of support. The position of the subject can be controlled by tilting the support, or by tilting the whole subject by means of a harness. In certain embodiments, the subject is tested while standing on foam. In certain embodiments, neck muscle vibration is further added during testing, according to standard methods readily appreciated by one of skill in the art. In certain embodiments, vibration is applied to the left or right dorsal neck or left or right mastoid.

In another embodiment, the present invention provides a method for diagnosing otolith dysfunction. The method includes: providing a subject with eyewear capable of displaying an image, displaying an image on the eyewear at an angle to the gravitational vertical; measuring and recording the position and movement of the subject's head in response to the image using a processor, and diagnosing the subject with otolith dysfunction if the subject has an abnormal response, or diagnosing the subject as having normal otolith function if the subject has a normal response. In certain embodiments, the subject is isolated from visual stimuli, apart from the image. In various embodiments, successive images are displayed periodically, at angles from the gravitational vertical, and the subject's response to each image is measured. In certain embodiments, the movement and position of the subject's head is tracked and recorded with an electronic tracking device.

In some embodiments the invention teaches a method for assessing a level of compensation for otolith dysfunction in a subject who has undergone rehabilitation, including: providing a subject who has undergone rehabilitation with eyewear capable of displaying an image; displaying an image on the eyewear at an angle to the gravitational vertical; measuring and recording the position and movement of the subject's head in response to the image using a processor; and assessing the level of compensation for otolith dysfunction in the subject, based upon the subject's response.

In another embodiment, the present invention provides a method for tracking one or both eyes of a subject while measuring a subject's head tilt response. In certain embodiments, the information determined by tracking a subject's eyes is used to determine the role of a subject's eyes in his perception of the gravitational vertical. In certain embodiments, ocular tilt and/or skew deviation are determined based upon the tracked eye movements. In certain embodiments, the eye movements tracked include those made horizontally and/or vertically and/or the rotations performed by the eyes. One of skill in the art would readily appreciate that there are many ways to track eye motion in a subject Merely by way of example, eye tracking can include electrodes as in electrooculography, where the potentials obtained from the electrodes placed next to the eyes give the position of each eye. In certain embodiments of the invention, eye tracking is accomplished with video tracking, in which a camera is mounted on the head mounted display and used to record the eyes. In these embodiments, software processes the images obtained to track the eye movements. In certain embodiments, a head mounted display is used as a base to mount cameras and track the eyes simultaneously with the head tracking to find correlations between the two types of responses.

In certain embodiments, one or more of the inventive methods described herein are used to determine the presence or absence of a vestibular disorder, wherein the presence of a vestibular disorder is determined if the test results are abnormal compared to a range of values derived from a group of individuals without vestibular disorders. In certain embodiments, abnormal test results generally indicate vestibular hypofunction. In an embodiment, the vestibular disorder is caused by a perilymphatic fistula. In an embodiment, the vestibular disorder is caused by vestibular neuronitis. In certain embodiments, the vestibular disorder is selected from the group consisting of: Meniere Disease, vestibular neuronitis, recurrent vestibulopathy, ototoxicity, labyrinthine trauma, cochleovestibular infarct, perilymphatic fistula, acoustic neuroma, laberinthytis, and combinations thereof.

In some embodiments, the subjects are also tested in a manner selected from the group consisting of: bed side examination, electronystagmography (ENG), auditory testing, CT scanning, and combinations thereof. In certain embodiments, a subject tested is between the ages of 2 years old and 100 years old. In certain embodiments, the subject has the mental capacity to appreciate his or her actions and to follow directions. In certain embodiments, the subject tested is diagnosed with unilateral vestibular loss. In other embodiments, the subject tested is diagnosed with bilateral vestibular loss.

In still another embodiment, the present invention provides a device for determining a subject's perception of the gravitational vertical, the device including: virtual reality goggles capable of displaying an image, an electronic means for generating the image; an electronic means for monitoring and recording the motion and position of the subject's head; and an electronic means for monitoring and/or recording the motion and position of the subject's eyes in response to the image.

In certain embodiments, the present invention provides a system for determining a subject's perception of the gravitational vertical. The system includes: virtual reality goggles configured to display an image at an angle to the gravitational vertical; an electronic means for generating the image, an electronic means for measuring and recording the motion and position of the subject's head in response to the image, a data storage comprising a head motion and position capturing and analyzing application, and a processor operatively coupled to: the electronic means for measuring and recording the motion and position of the subject's head in response to the image, the virtual reality goggles, and the electronic means for generating the image, wherein, upon execution, the electronic means for generating the image generates the image, the virtual reality goggles display the image, and the electronic means for recording the motion and position of the subjects head in response to the image records the motion and position of the subject's head, and a subject's perception of the gravitational vertical is determined. In some embodiments, the system also includes a means for tracking the motion of a subject's eyes and an eye motion tracking application, wherein the processor is further operatively coupled to the means for tracking the motion of the subject's eyes, and wherein upon execution, the means for tracking the motion of the subject's eyes tracks the motion of the subject's eyes.

One of ordinary skill in the art would appreciate the head mounted display could easily be substituted by a regular monitor, including LCD, LED, flat screen, projector and other types capable of displaying an image. When a regular monitor is used, the information obtained from the head tracking device is used not only to record the head position but also to re-orient the projected image. This re-orientation would provide a simulation of exactly the same situation perceived by a patient using virtual reality goggles, but using a fixed display.

In certain embodiments, the experimentation could be performed using a desktop or laptop computer with a video camera integrated therein. The computer could be configured with software that would allow the integrated video camera to simultaneously track head and/or eye motion and position while re-orienting the image displayed on the screen.

One of skill in the art would further appreciate the methods disclosed herein are not limited to normal gravity conditions but may also be applied in circumstances in which gravity is lessened, such as in a simulator. Likewise, the test could be performed under conditions of zero gravity, during space missions or on space stations.

In certain embodiments, the invention teaches a computer readable medium having computer-executable components that, when executed by a computing device operatively coupled to: virtual reality goggles capable of displaying an image, an electronic means for generating the image, one or more electronic means for measuring and recording the motion and position of the subject's head and/or eyes in response to the image, cause: the virtual reality goggles to display an image at an angle to the gravitational vertical; the means for measuring and recording the motion and position of the subject's head and/or eyes to measure and record the position and motion of the subject's head and/or eyes in response to the image; and the computing device to determine parameters related to the subject's response to the image, based upon the measurements. In certain embodiments, the parameters determined are selected from the group consisting of: steady state error (SSE), delay time (TDT), rise time (TRS), settling time (TST), overshoot (OSP), integral time square absolute error (IT2AE) and combinations thereof.

EXAMPLES

Example 1

Subjects

Twenty eight normal subjects without any history of vestibular disorders were assessed (F: 19, M:9, mean age: 30). Five patients (F: 5, mean age: 56.6) with vestibular disorders studied with bed side examination, electronystagmography (ENG), auditory testing and evaluation by CT scan images, as well as the HTR test. The patient population included 4 unilateral (UVL) and 1 bilateral vestibular loss (BVL). The five patients showed vestibular hypofunction performed by caloric testing and clinical features related to the UVL and BVL (Table 1).

TABLE 1

Characteristics of patients with vestibular disorders

| Patient | Disorder | Ear | Age | Gender | Onset |
|---|---|---|---|---|---|
| 1 | UVL (Perilymphatic fistula) | R | 52 | F | 2 weeks |
| 2 | UVL (Vestibular neuronitis) | R | 67 | F | 4 weeks |
| 3 | UVL (Vestibular neuronitis) | L | 56 | F | 2 weeks |
| 4 | BVL (Ototoxicity) | — | 51 | F | 2 years |
| 5 | UVL (PANS)* | R | 57 | F | 6 weeks |

*Post Acoustic Neurinoma Surgery

While not wishing to be bound by any particular theory, because the populations were below 70 years old, aging of end organs was probably not a significant factor.

Example 2

Experimental Setup

Test Description

Each subject stood on a firm horizontal surface wearing virtual reality goggles (Z800 3Dvisor, eMagin) and a light isolator to ensure that no external visual references were available. Subjects were then solely exposed to the visual stimulus displayed on the goggles. A head tracking device (InertiaCube2+, Intersense) was attached to the goggles to keep record of the angle of the subject's head. Stimulation and recording was accomplished by means of custom made software. The stimulus displayed on the goggles was a white stripe presented over a black background.

Each subject was presented with the stimulus on virtual reality goggles (Head Mounted Display, HMD) and was asked to tilt his or her head to align the bar with their GV (FIG. 1). All subjects were instructed to align the bar as soon as a new image appeared on the goggles. When the exercise started, a stripe was presented with a certain inclination for a specific amount of time, and then a new stripe with a different orientation appeared on the screen. When the subject perceived that the white stripe was aligned with the GV he or she was instructed to remain in that position until a new bar appeared on the display. When the screen went black, the trial was over. This process was repeated 5 times with the same parameters. The test took approximately 5 minutes. Head inclination was recorded at 50 Hz. The stimulation paradigm, shown in table 2, was designed to cover small and large tilt angles and suitable amounts of time to respond.

TABLE 2

Stimulation Protocol.

| Inclination of the bar in each step (degrees) | Step Duration (seconds) |
|---|---|
| 25 | 5 |
| −25 | 3 |
| −15 | 6 |
| 35 | 4 |

Having the goggles aligned with the horizontal, each positive angle demands tilting the head such degrees towards the right shoulder to align the stripe to the GV.

To characterize the HTR dynamic response, six parameters were extracted:

Steady state error (SSE)—Steady state angle error between the bar position and head position as a percentage of the step.

Delay time (TDT)—Time (in seconds) it takes for the subject to react to a step in the bar angle.

Rise time (TRS)—Time (in seconds) it takes for the subject to move his head from 5% to 95% of the bar step.

Settling time (TST)—Time (in seconds) to reach a steady state angle within 2%.

Overshoot (OSP)—Some subjects may overreact to a bar angle change and tilt their heads a larger angle than necessary before coming down to the right value. The value of this maximum head tilt as a percentage of the right angle needed is usually called overshoot.

Integral time square absolute error (IT2AE)—This parameter takes into account the error between the white bar and head tilt angle all through the step according to the following equation:

$$IT2AE = \frac{1}{T}\int_0^T t^2 e^{-\lambda t} |wb(t) - ht(t)| dt$$

In this equation, wb(t) and ht(t) are the white bar and head tilt angle positions respectively. The time factor inside the integral represents a weighting of the error selected to diminish the error at the beginning and end of each step where T is the step duration and $\lambda$ was set to 1. Large values of TDT, OSP and TRS will have a big contribution to the IT2AE since they reflect large differences in |wb(t)−ht(t)| when the weighting function presents larger values.

Figure 2:
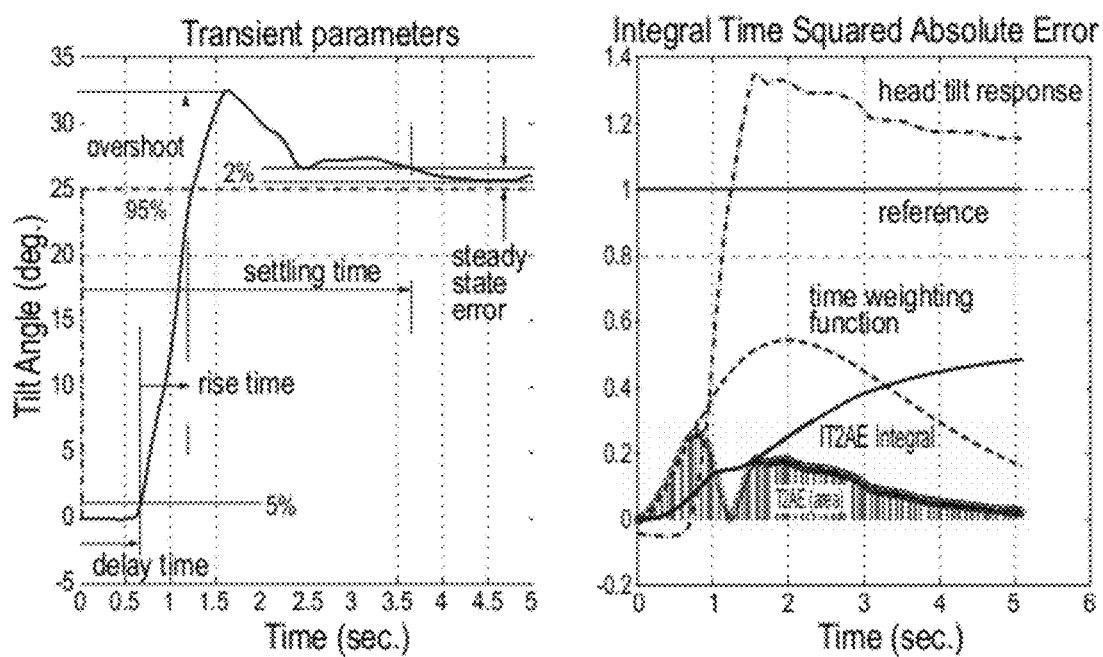
FIG. 2 demonstrates, in accordance with an embodiment of the invention, a sample of a step response showing the dynamic parameters, including: steady state error (SSE), delay time (TDT), rise time (TRS), settling time (TST) and overshoot (OSP) (left). On the right, the dashed line shows the shape of the "weighting function" selected and the shadowed region represents the IT2AE parameter.

The first five parameters are shown in FIG. 2 (left). They are commonly used to characterize a dynamical system step response [15]. The last parameter is represented in FIG. 2 (right). It is commonly used in control theory as a performance index to compare the behavior of closed loop systems [9].

The format of the HTR experiment means that five sets of six parameters each were obtained per step and per subject. Mean value and standard deviation were calculated for each of the six parameters to generate two unique six dimensional vectors of parameters for each individual. Step three was not considered for evaluation of mean and standard deviation since the step was too small to allow the subjects to adjust their respective head angles. Therefore, the six parameters defined were computed for 3 steps (one was discarded) and 5 trials, giving a sample of 15 values per parameter and per subject. From these values, mean and standard deviations per parameter that characterize a subject were found. For the 28 mean and standard deviation values that characterized the population of normal subjects per parameter, mean and confidence intervals were found. All the parameters were checked against a normal distribution using the Kolmogorov-Smirnov (K-S) test (alpha=5%) and finding its mean and confidence intervals. The set of vectors obtained for the whole population of normal subjects were analyzed to find relationships and cues that may characterize a normal subject's response to this experiment.

The responses of five patients with vestibular end organs hypofunction were also assessed with HTR and the same six parameters were obtained and compared with the population of normal subjects to detect if significant differences could be found using box-whisker and 3-sigma plots [16].

Example 3

Results

Figure 3:
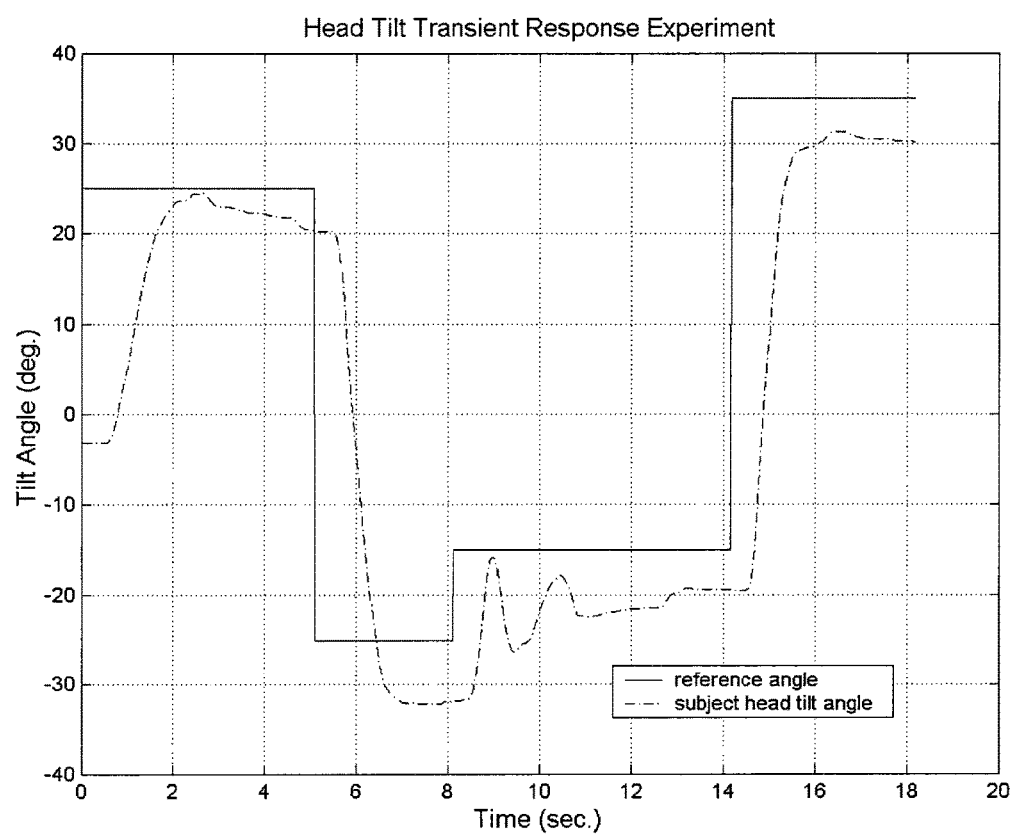
FIG. 3 demonstrates, in accordance with an embodiment of the invention, a typical response of a subject. The solid line shows the angle of the bar while the dashed line shows the angle of the head.

FIG. 3 shows a typical HTR response for a normal subject along the whole trial while Table 3 shows the mean value, standard deviation and confidence intervals obtained for the six parameters considered.

TABLE 3

Parameter characteristics obtained for normal subjects.

|  | SSE (%) | TDT (sec) | TRS (sec) | TST (sec) | OSP (%) | IT2AE |
|---|---|---|---|---|---|---|
| Mean Value: | −0.371 | 0.60163 | 1.19900 | 2.00524 | 5.592 | 0.08867 |
| Mean Confidence Interval (95%): |  |  |  |  |  |  |
| Min: | −3.992 | 0.57458 | 1.04413 | 1.82435 | 3.809 | 0.07881 |
| Max: | 3.249 | 0.62868 | 1.35388 | 2.18613 | 7.376 | 0.09853 |
| Standard Deviation: (SD) | 9.337 | 0.06976 | 0.39941 | 0.46651 | 4.600 | 0.02543 |
| SD Confidence Interval (95%)*: |  |  |  |  |  |  |
| Min: | 7.382 | 0.05515 | 0.31578 | 0.36883 | 3.637 | 0.02010 |
| Max: | 12.708 | 0.09495 | 0.54365 | 0.63498 | 6.261 | 0.03461 |

Each parameter was calculated in 3 steps and 5 trials giving a sample of 15 values per parameter. From these values mean and standard deviation that characterize a subject for each parameter were calculated. For the 28 mean values, mean and confidence interval were found, and likewise for the 28 standard deviation values.

Figure 4:
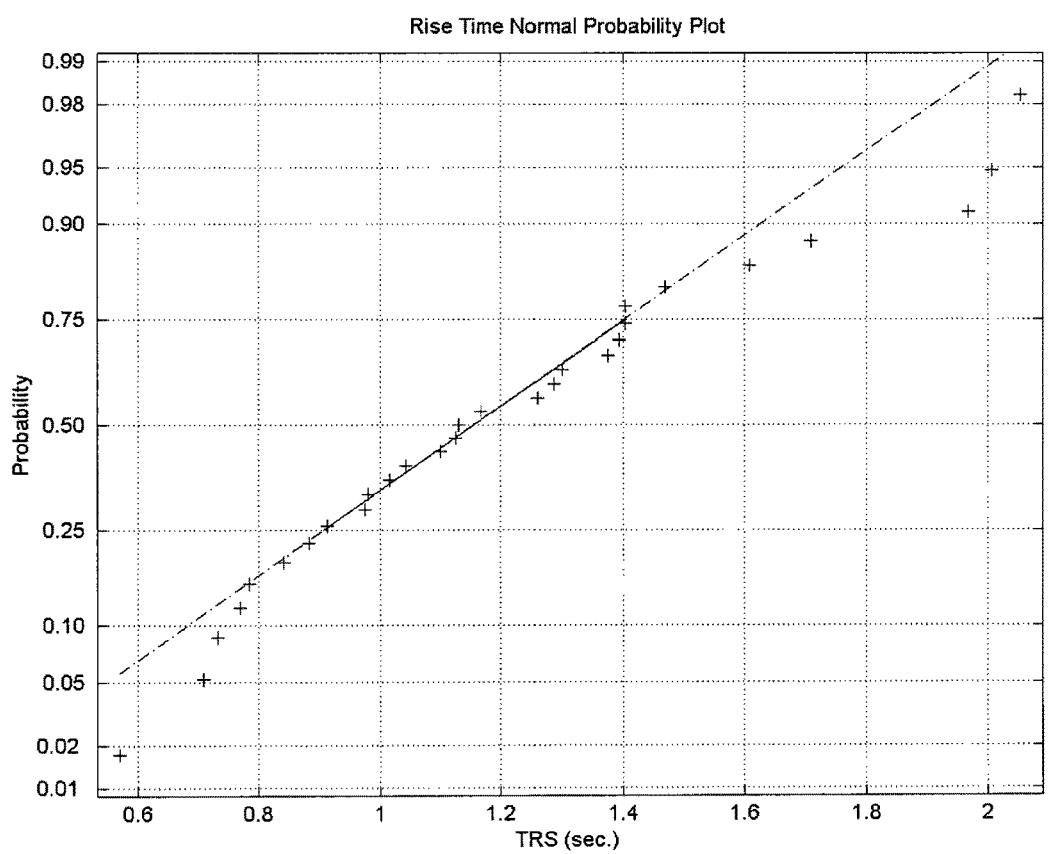
FIG. 4 demonstrates, in accordance with an embodiment of the invention, a rise time normal probability plot.

All parameters matched with a normal distribution using K-S (0.5<p<0.97). Rise time (TRS) samples and their adjustment with a normal distribution can be seen in FIG. 4. A similar plot can be found for all parameters.

Figure 5:
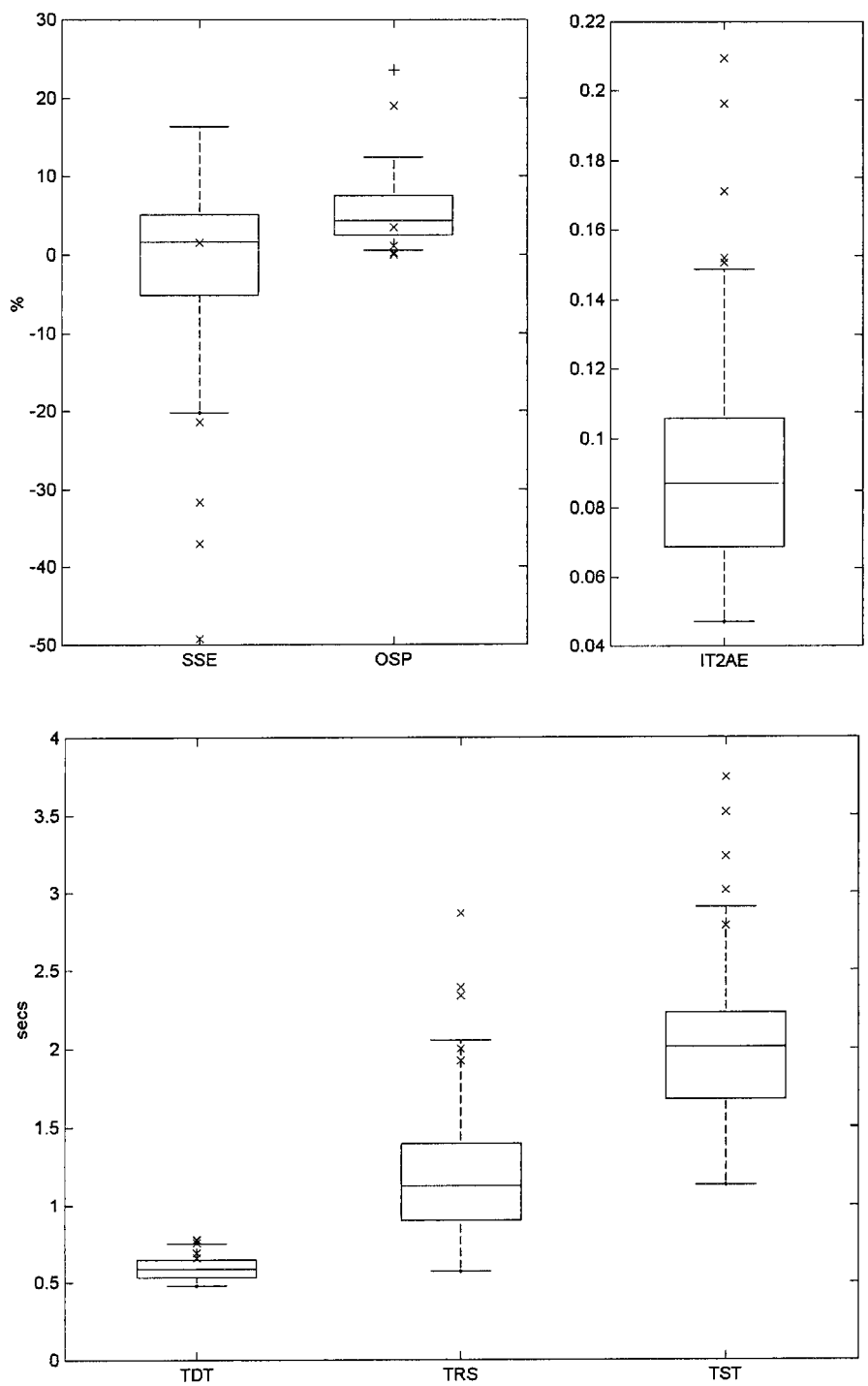
FIG. 5 demonstrates, in accordance with an embodiment of the invention, a box-whisker plot of all parameters for the normal subjects showing the median (horizontal line in each box), interval (dotted lines), outliers (+) and the results of each pathological subject (x). This is a one dimensional plot of the results.
Figure 6:
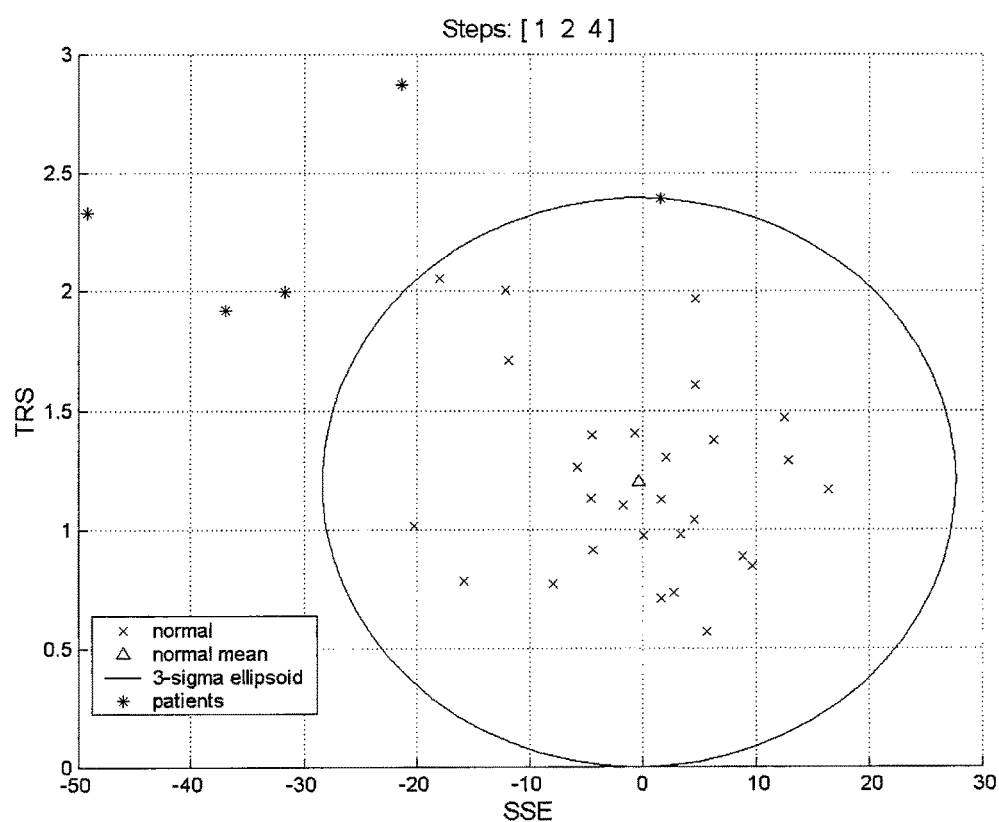
FIG. 6 demonstrates, in accordance with an embodiment of the invention, a two dimensional plot between SSE and TRS. A 3-sigma ellipsoid is plotted in the same figure showing all normal subjects fitting inside the ellipsoid and all except one of the patients outside.

In order to visualize the distribution of the results, the normal population was plotted in a box-whisker plot together with the results from the pathological population in FIG. 5. SSE and TRS were found to characterize the transient response of the system. FIG. 6 shows a two dimensional plot between SSE and TRS. A 3-sigma ellipsoid is plotted in the same figure showing all normal subjects fitting inside while all but one of the patients were outside the ellipsoid.

When HTR was performed on patients, except for SSE and OSP, all parameters for all patients were found to be outside the mean confidence intervals evaluated for normal subjects (Table 4).

TABLE 4

Mean value of HTR parameters found for patients tested.

| Patient | SSE (%) | TDT (sec) | TRS (sec) | TST (sec) | OSP (%) | IT2AE |
|---|---|---|---|---|---|---|
| 1 | −31.647 | 0.77551 | 1.99747 | 3.01825 | 1.077 | 0.17120 |
| 2 | 1.507 | 0.66074 | 2.39259 | 3.23407 | 19.005 | 0.15076 |
| 3 | −49.206 | 0.78225 | 2.33333 | 3.52149 | 0.034 | 0.20935 |

TABLE 4-continued

Mean value of HTR parameters found for patients tested.

| Patient | SSE (%) | TDT (sec) | TRS (sec) | TST (sec) | OSP (%) | IT2AE |
|---|---|---|---|---|---|---|
| 4 | −36.961 | 0.76080 | 1.92111 | 2.79061 | 3.518 | 0.19652 |
| 5 | −21.393 | 0.69032 | 2.87277 | 3.74374 | 0.180 | 0.15208 |

Figure 7:
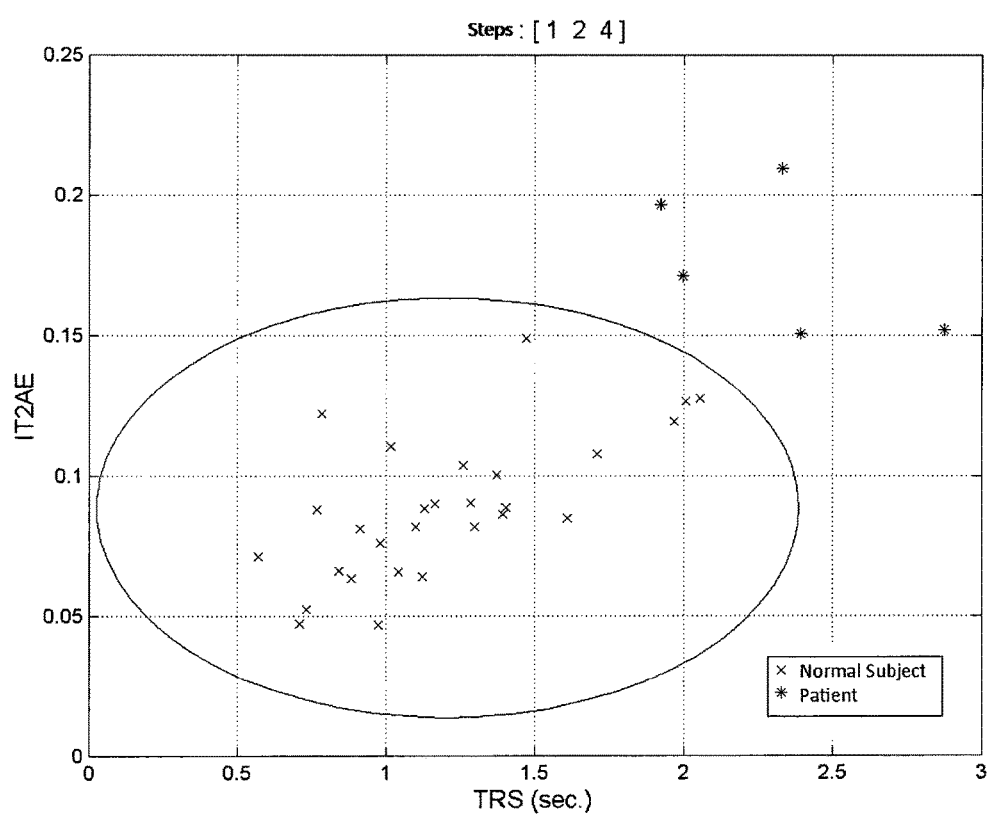
FIG. 7 demonstrates, in accordance with an embodiment of the invention, a two dimensional plot showing IT2AE vs. TRS and the 3-sigma ellipsoid. All normal subjects are inside the ellipsoid while pathological patients fall outside.

Comparing TRS and IT2AE, it can be observed that the parameters found for patients lay outside the 3-sigma ellipsoid found for the normal subjects' distribution of data (FIG. 7).

Example 4

Discussion

In the SVV the subject adjusts the angle of a light bar, rotating it until it is perceived as vertical (while subjects head is kept in upright or tilted position) [21]. In HTR experiments subjects move the whole visual scene (composed solely by a white stripe) by tilting their heads. This presents two main differences: 1) the vestibular end organs (VEO) information and neck proprioceptive afference are continuously varying and 2) the visual stimulation the eyes receive is constant.

Because in the SVV, the head is always kept in the same position (upright or tilted position), VEO information is always the same, whether, in the case of normal population, there is a symmetric (upright head position) or an asymmetric (head tilted) firing rate. This VEO information is constant along the entire trial. In the HTR experiment, the subject is constantly rotating his head in the roll plane and thus, dynamically changing the information the brain receives.

Another difference is that while in the SVV the visual information is dynamic, in the HTR test it is static. In the SVV the light bar is rotated, and so, the retinal image perceived varies with each rotation. In the HTR test, since the image is displayed on the goggles (attached to the head) the retinal image is basically the same for each step. These two methods (SVV and HTR) can be regarded as complementary in terms of how the information involved varies (visual, vestibular and neck proprioception).

Normal subjects seem to present very similar TDT, almost no OSP and relatively small SSE with a large dispersion. Although TDT is an important property of dynamic systems in general, in this case it does not reflect a vestibular response, but more likely a reaction time to a visual input and subject task execution. Also, TST and TRS, roughly contain the same information due to their strong correlation (r=0.97) and can be used interchangeably to characterize the HTR.

While not wishing to be bound by any particular theory, the fact that TRS is larger in patients seems to indicate that having less or distorted vestibular end organ input requires more time to estimate the GV, perhaps by using other sources of information to compensate the peripheral lesion. It has been shown that neck afference plays a significant role in how the central nervous system compensates the vestibular end organ deficit [19]. When exploring the perception of horizontal during mastoid and neck vibration in normal and UVL subjects, it was shown that the stimulation of neck spindles through its vibration produced an asymmetry in the response of the UVL subjects. This was not seen when the mastoid was stimulated in UVL patients and when the neck was stimulated in normal subjects [11]. While not wishing to be bound by any particular theory, it seems likely that the delay to reach the perceived verticality of the bar observed in the vestibulopathic subjects from the inventors' study may represent evidence of the lack of a full sensory substitution for the vestibular loss.

FIG. 5 shows that, based on just one parameter, only IT2AE is able to successfully discriminate between populations. On the other hand, by selecting an appropriate combination of two parameters, discrimination is easier to see and becomes more robust.

While not wishing to be bound by any particular theory, these results may also suggest that SSE and TRS parameters may characterize the transient response of subjects in this experiment and the evaluation of this phenomenon could be useful in the assessment of vestibular and balance disorders.

Example 5

Methods

Subjects

Thirty two normal subjects without any history of vestibular disorders were assessed (F: 21, M:11, mean age:32) for a static test. To generate the dynamic models of the response twenty eight normal subjects with the same health conditions as the previous group were assessed (F: 19, M: 9, mean: 30).

Example 6

Experimental Setup

Test Description

Each subject tested stood on a firm horizontal surface wearing virtual reality goggles (Z800 3Dvisor, eMagin) and a light isolator to ensure that no external visual references were available. Subjects were only exposed to the stimulus displayed on the goggles. A head tracking device (InertiaCube2+, Intersense) was attached to the goggles to keep a record of the angle of the head. Stimulation and recording was done by means of custom made software. The stimulus displayed on the goggles was a white stripe presented over a black background.

Example 7

Static Test (sHTR)

Figure 8:
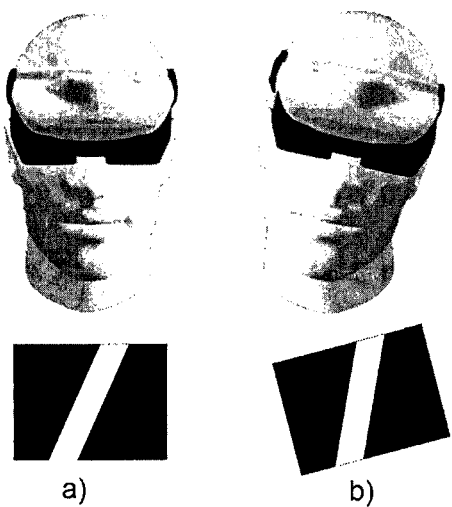
FIG. 8 demonstrates, in accordance with an embodiment of the invention: a) a subject with his head in an upright position and the image seen on the goggles presenting the white stripe over a black background; and b) a subject with his head tilted slightly. The white stripe is close to the GV but has not yet reached it. Images are as seen by the subject.

Subjects were presented with the stimulus on the virtual reality goggles (Head Mounted Display, HMD) and they were asked to tilt their heads to align the bar with their GV (FIG. 8). When the exercise started, a stripe was presented with 30 degree inclination and when each subject perceived that the white stripe was aligned with the GV he or she remained in that position and reported it the technician. The technician pressed the keyboard for the angle to be stored. Then a new stripe with a different orientation appeared on screen (same angle but tilted to the other side). The subject aligned the stripe to the GV, acknowledged his or her perception of such and the angle was stored. Afterwards, the screen went black, the patient recovered with his head in an upright position and the trial is over. This process was repeated 10 times with the same parameters with the whole test taking approximately 5 minutes. Having the goggles aligned with the horizontal, a positive angle of 30 degrees demands tilting the head that number of degrees towards the right shoulder to align the stripe to the GV, and a negative angle implies a roll tilt towards the left shoulder.

Example 8

Dynamic Test (dHTR)

For this test subjects were presented with the stimulus on the virtual reality goggles and they were asked to tilt their heads to align the bar with their GV. All subjects were instructed to align the bar as soon as a new image appeared on the goggles. When the exercise started, a stripe was presented with a certain inclination for a specific amount of time, and then a new stripe with a different orientation appeared on the screen. When each subject perceived that the white stripe was aligned with their GV he or she remained in that position until a new bar appeared on the display. When the screen went black, the trial was over. This process was repeated 5 times with the same parameters, and the whole test took approximately 5 minutes. Head inclination was recorded at 50 Hz. The stimulation paradigm, shown in table 5, was designed to cover small and large tilt angles and suitable amounts of time to respond.

TABLE 5

Stimulation protocol in dHTR.

| Bar Inclination (degrees) | Step Duration (seconds) |
|---|---|
| 25 | 5 |
| −25 | 3 |
| −15 | 6 |
| 35 | 4 |

Example 9

Studied Parameters and Statistics

Since there was no method of determining that the head tracking device was perfectly aligned with the goggles, the inventors did not use absolute values in this instance, as these may have been biased. However, the alignment can be determined by positioning the head in an upright position and zeroing the measurement from the accelerometer to compensate for any deviations.

The excursion used in sHTR involved the total range for positive and negative angles in each trial. Since each side demanded a 30 degree inclination, excursions of 60 degrees were expected and the initial position did not influence the results. The inventors used the mean of the 10 results for each subject, thus having a vector of 32 mean values. Statistical analysis of the results was performed to check normality and eliminate outliers. For the dHTR experimental data, a discrete linear model of the following form was found for each subject:

$$A(q)y[k]=B(q)u[k-nk]+C(q)e[k]$$

Where u[k] is the reference signal, y[k] is the head tilt angle estimation, and e[k] is the observation error at time step k. A(q), B(q) and C(q) are polynomials of the delay operator $q^{-1}$ and nk is the step delay. The parameters of the polynomials and nk were found using an iterative recursive LMS algorithm [19] to best match the actual response for each subject. The models obtained using dHTR data were used to predict the results of a sHTR experiment on those subjects.

If, $A(q) = 1 - \sum_{k=1}^{na} a_k q^{-k}$, $B(q) = \sum_{k=1}^{nb} b_k q^{-k}$, $C(q) = \sum_{k=1}^{nc} c_k q^{-k}$ the steady state peak to peak angle for the sHTR experiment is:

$$\alpha_{pp} = 2\alpha \frac{\sum_{k=1}^{nb} b_k}{1 - \sum_{k=1}^{na} a_k}, \alpha = 30° \quad (1)$$

Statistical analysis of the peak to peak angle for all subjects was performed to compare with the sHTR results.

Example 10

Results

Figure 9:
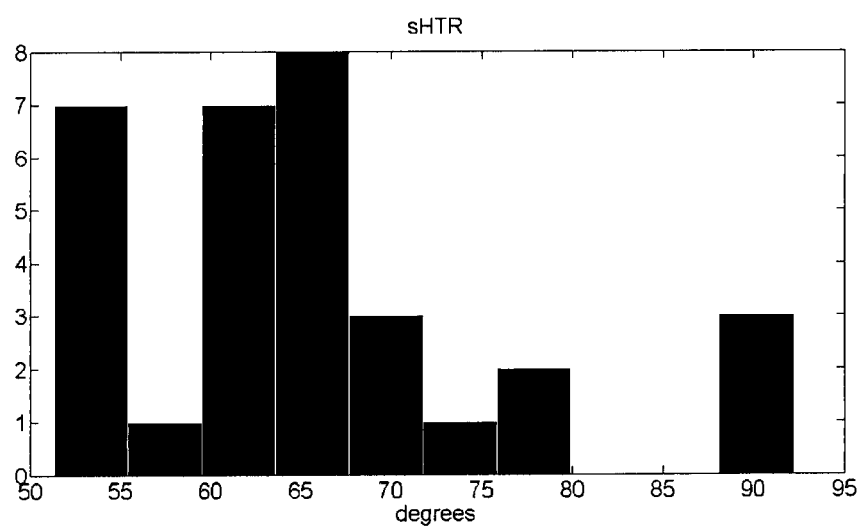
FIG. 9 demonstrates, in accordance with an embodiment of the invention, a histogram for the mean excursion of the ten trials of each subject for the sHTR test.

For the sHTR test the excursion had a mean of 65.6 degrees (min: 51.4, max: 92.2). FIG. 9 shows a histogram of the results.

Figure 10:
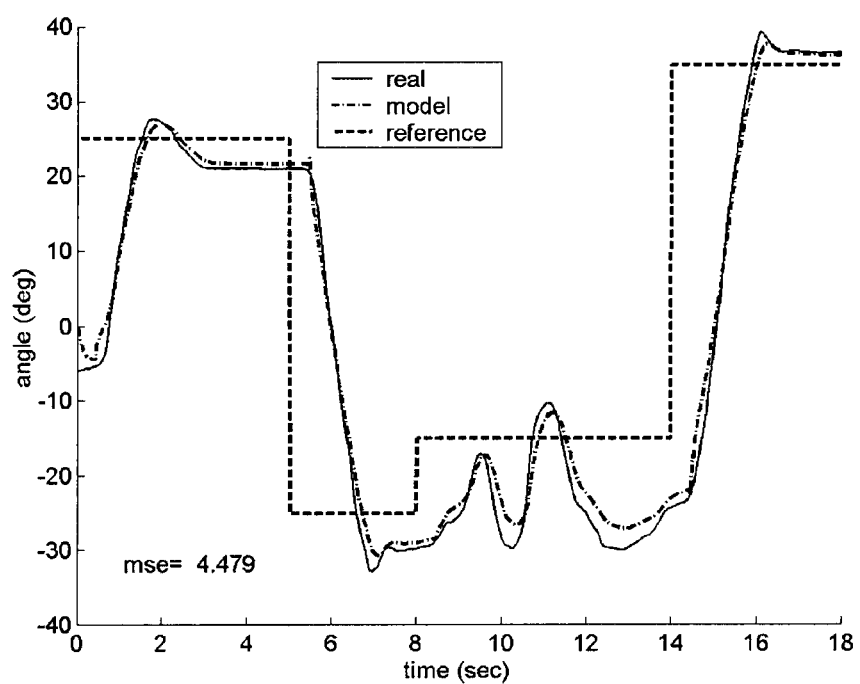
FIG. 10 demonstrates, in accordance with an embodiment of the invention, a typical dHTR response for a subject comparing the actual response with the best model obtained.

In the case of the dHTR data, the best models found have:

na=3, nb=3, nc=2, nk=20, for almost all cases, with a compromise for a small mean squared error without overfitting the data. In a couple of subjects a slightly smaller error was found for na=2 but it was not significant and the preference was to use the same model order in all cases. FIG. 10 shows a typical dHTR response for a normal subject and the fit obtained with the model.

Figure 11:
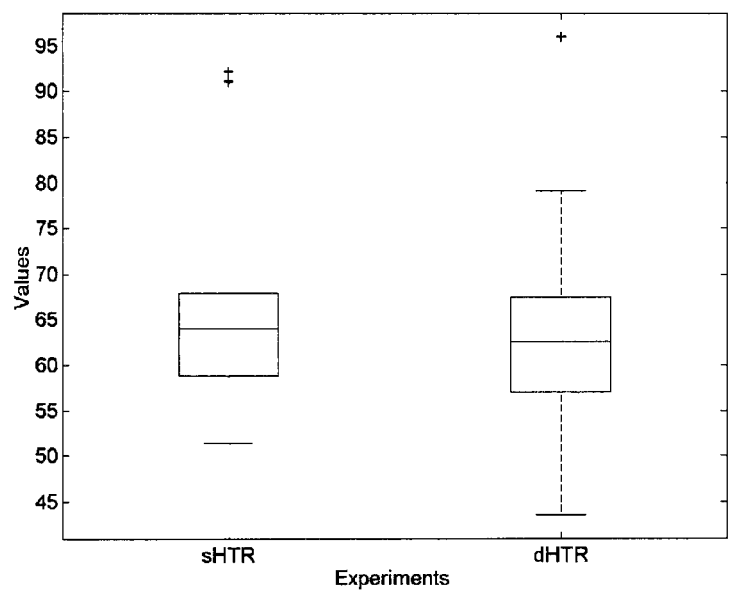
FIG. 11 demonstrates, in accordance with an embodiment of the invention, a boxplot of sHTR data and $\alpha_{pp}$ found for dHTR subjects.

With the models generated and using equation (1), an estimation of the values of $\alpha_{pp}$ for all subjects was found. Also, the values of $\alpha_{pp}$ were tested against a normal distribution using a Wilcoxon test with a good fit (mean=62.58 deg, std=10.88, P=0.57, $\alpha$=0.05). To compare dHTR and sHTR data a boxplot of $\alpha_{pp}$ and the mean values of the excursions obtained for the sHTR population were found, as demonstrated in FIG. 11.

Figure 12:
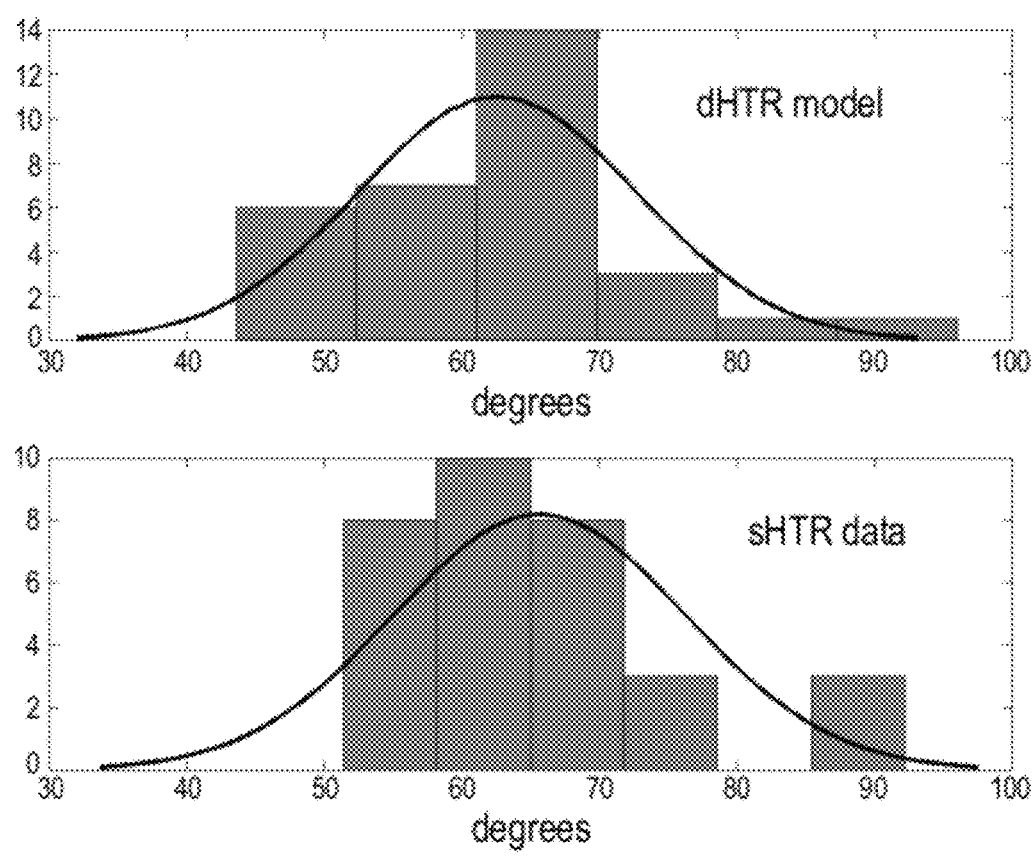
FIG. 12 demonstrates, in accordance with an embodiment of the invention, a histogram of sHTR data and $\alpha_{pp}$ found for dHTR subjects showing best normal probability fit.
Figure 13:
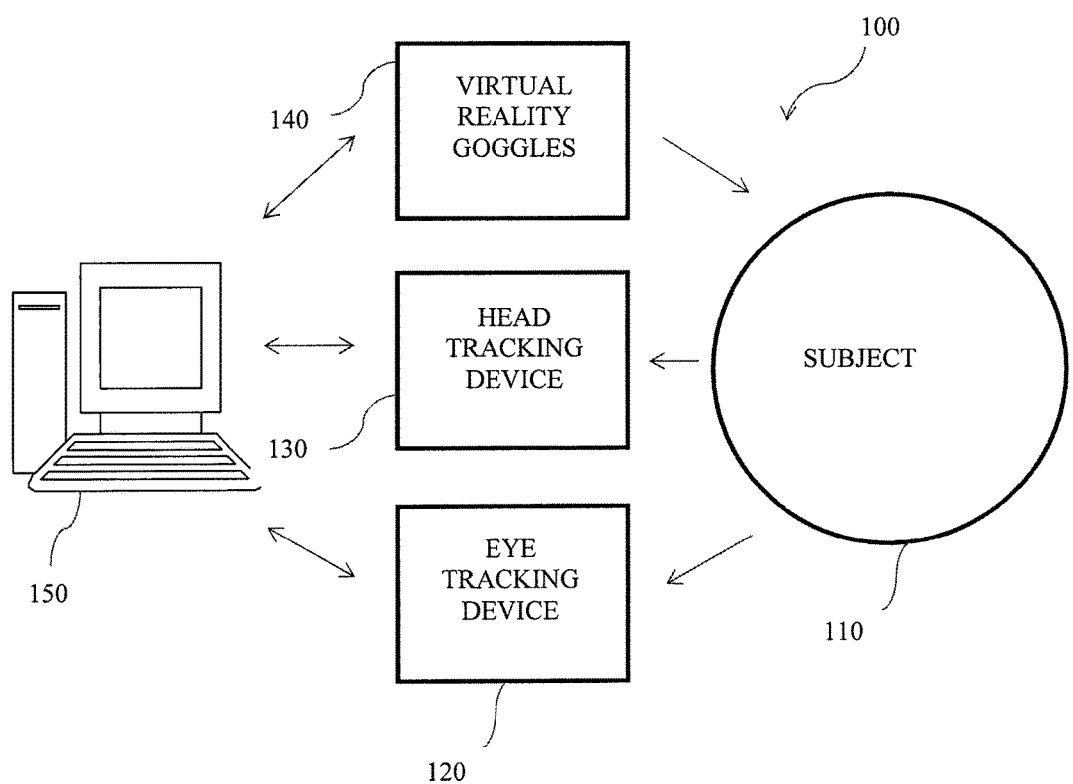
FIG. 13 demonstrates, in accordance with an embodiment of the invention, a block diagram of a system for detecting a subject's perception of the gravitational vertical.

The Wilcoxon test was also used to investigate if the two series of data for peak to peak values were statistically similar. With all data values the test was found to be true with P=0.398, $\alpha$=0.05. Elimination of the outlier values shown in FIG. 10 implies that the fit between the two series of data reached P=0.774 for the same Wilcoxon test. FIG. 12 shows a histogram of both series together to visualize their similarities and differences.

Example 11

Discussion

Two different experiments were conducted using the same experimental setup. A dynamic transient response named dHTR and a steady state version called sHTR. From the dHTR data a linear dynamic model was found for each subject that was able to reproduce the results of the sHTR experimental data in a statistical sense. The dynamic models obtained may be used to extract other parameters related to the transient response (e.g. overshoot, rise time, settling time) that also help in explaining the complex behavior of the GV perception in humans.

Example 12

Measurement Systems

Figure 14:
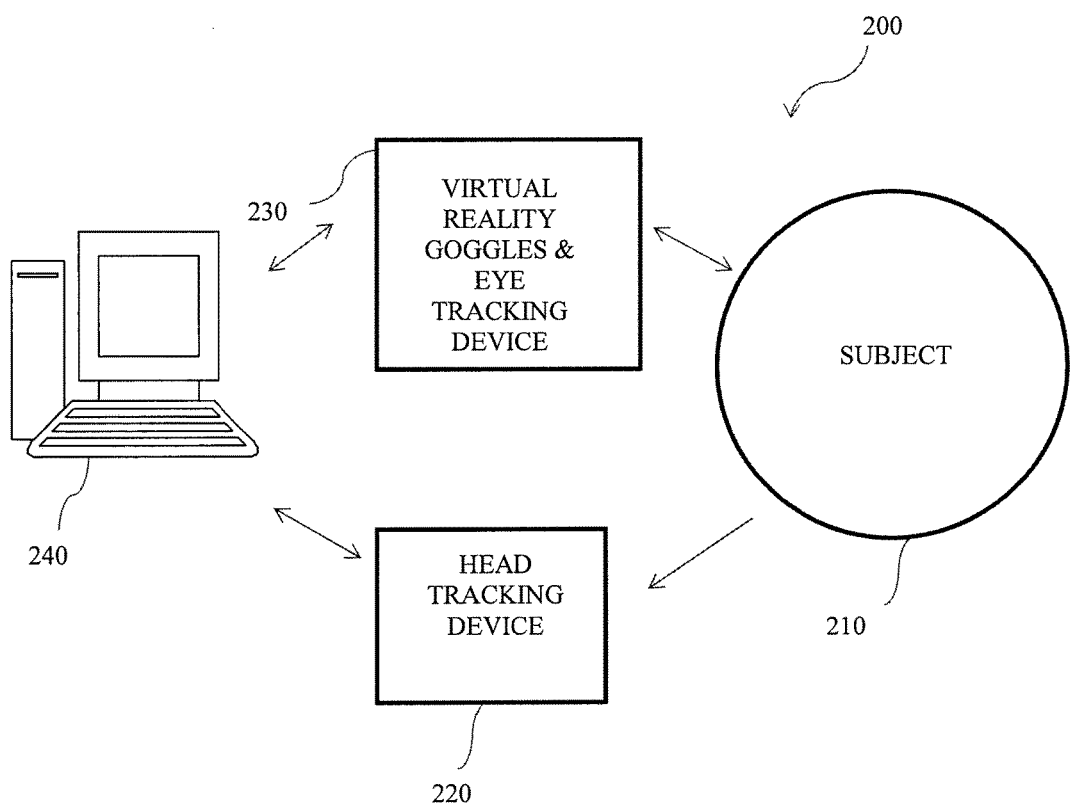
FIG. 14 demonstrates, in accordance with an embodiment of the invention, a block diagram of a system for detecting a subject's perception of the gravitational vertical.
Figure 15:
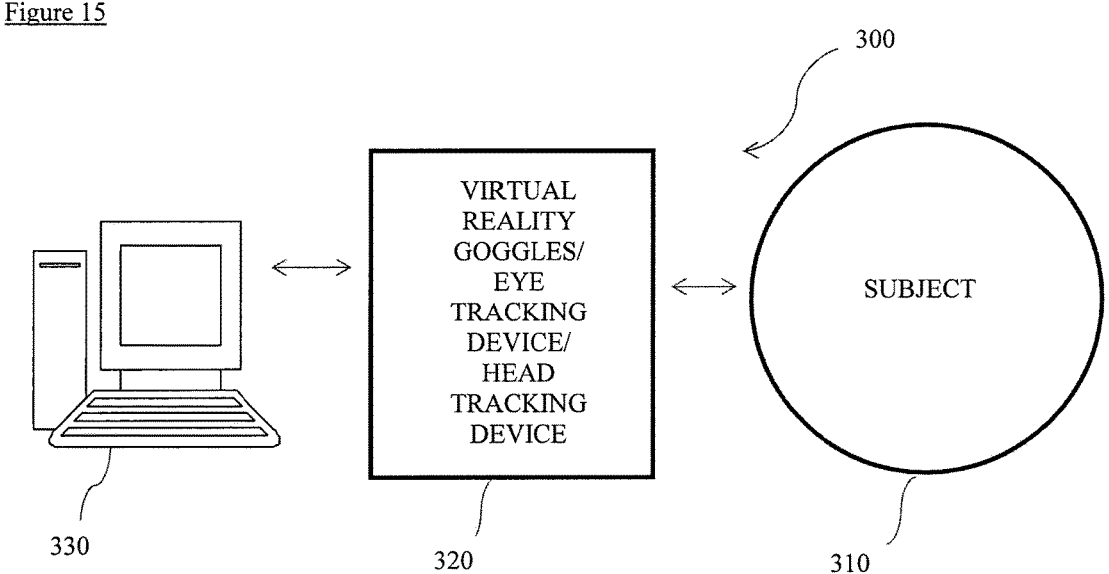
FIG. 15 demonstrates, in accordance with an embodiment of the invention, a block diagram of a system for detecting a subject's perception of the gravitational vertical.
Figure 16:
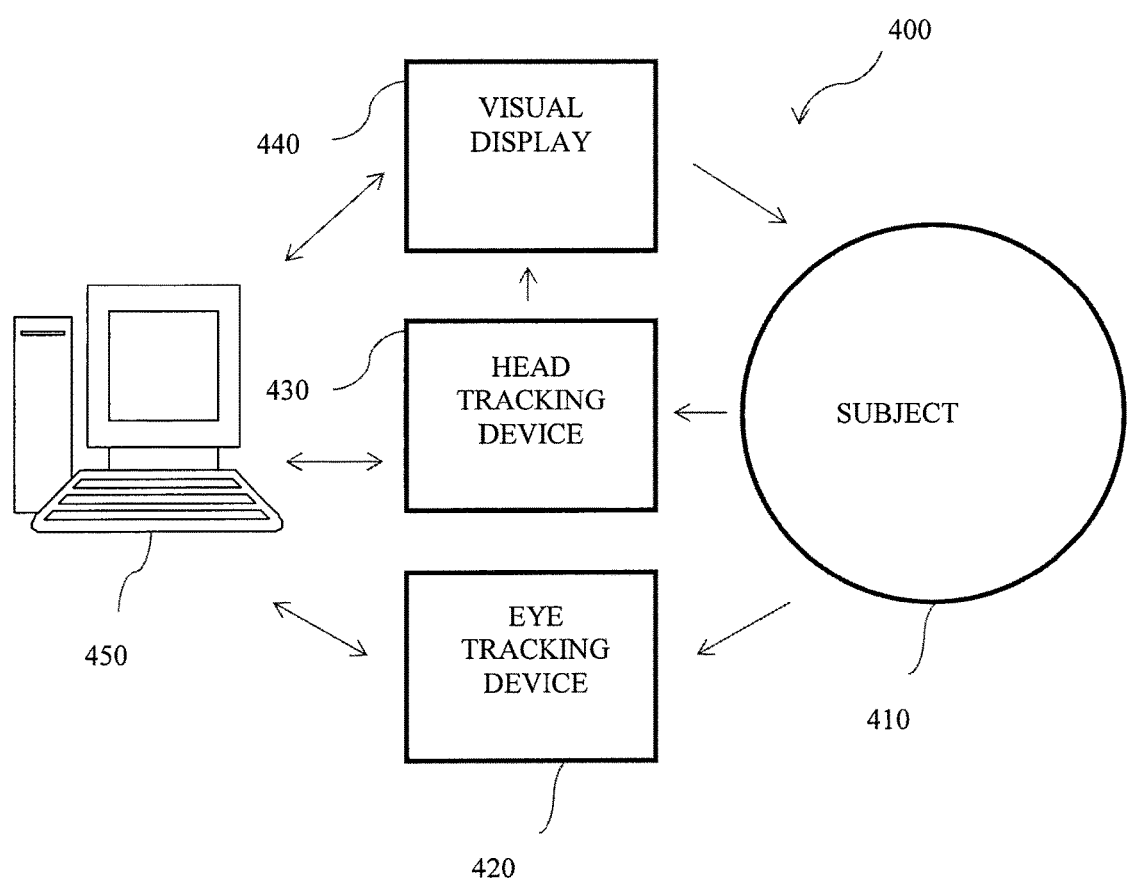
FIG. 16 demonstrates, in accordance with an embodiment of the invention, a block diagram of a system for detecting a subject's perception of the gravitational vertical.

FIGS. 13, 14, 15 and 16 are block diagrams demonstrating the relationship between various components of the system and a subject. As demonstrated in FIG. 13, the system 100 may include virtual reality goggles 120 for displaying an image, a head tracking device 130 for tracking a subject's head, an eye tracking device 140 for tracking a subject's 110 eyes, and a computing device 150 for analyzing the data generated by the individual components. FIGS. 14 and 15 demonstrate systems 200 and 300, in which components are integrated as indicated in 220, 230, and 320, respectively. FIG. 16 is a block diagram demonstrating a display 440 on which an image displayed is adjusted in real time using information from the head tracking device 430, so as to simulate the same experience as when virtual reality goggles 140 are used.

Example 13

Additional Experiments

Brief Summary

Rise time in the estimation of the gravitational vertical in the Head Tilt Response Test is increased in patients with peripheral vestibular lesions and residual chronic dizziness. The inventors assessed the perception of the gravitational vertical in patients with peripheral vestibular lesions through the head tilt response. The head tilt response was studied in 12 patients with peripheral vestibular lesions, 8 clinically with chronic dizziness and 4 without it. 23 normal subjects were studied as a control group. Two parameters of the head tilt response were assessed, rise time and steady state error, to characterize a dynamic system step response. A Kolmogorov-Smirnov test (alpha=5%) was used to verify normal distribution (steady state error p=0.53, rise time p=0.88). The three sigma ellipse was calculated for the control group. ROC curves were used to measure the sensitivity and specificity of these parameters. Rise time showed increased values in peripheral vestibular lesion patients with chronic dizziness. Two dimensional analysis (rise time vs. steady state error) allows a better discrimination between patients with peripheral vestibular hypofunction with chronic dizziness and the rest of the studied population.

Example 14

Introduction

Patients who had a sudden loss of information from the vestibular receptors (Meniere disease, vestibular neuronitis, etc), suffer "chronic dizziness" (CD) as a main disabling symptom after an acute stage. Similar complaints are described by patients who have unilateral or bilateral chronic vestibular hypofunction. The uncompensated vestibular hypofunction produces alterations in the stabilization of the image on the retina and a wrong estimation of the gravitational vertical (GV), generating a visual vertical perception disorder. Many reports have been published about the visual vertical perception in vestibular patients [1, 2, 3, 4] and also methods for its assessment [5, 6].

Figure 18:
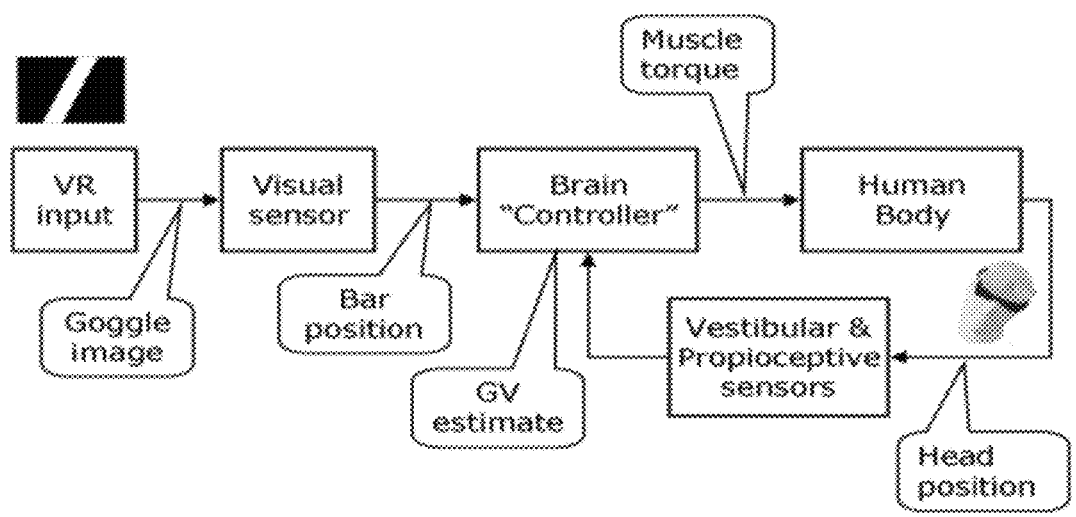
FIG. 18 demonstrates, in accordance with an embodiment of the invention, a block diagram for the HTR test specifying the main components and the information flow through the system. The visual stimulus is generated in the VR block and sensed by the subject's eyes giving an estimation of the bar angle relative to the GV. The Brain controller uses this information together with an estimation of the GV to generate corrective muscle torque actions to move the subject's head looking for the desired response.

As in the case of the aforementioned study previously disclosed in the examples, this study was performed to analyze the phenomenon of the GV perception in patients who have peripheral vestibular hypofunction (PVH) through an experiment called Head Tilt Response (HTR) [7, 8]. As previously disclosed herein, this test uses a dynamic approach in which subjects actively adjust their head position to match a visual stimulus to the GV. The analysis of the data involves considering the system as multi input (Visual, vestibular, somatosensory) and single output (Head tilt relative to GV). FIG. 18 shows a flow chart diagram of the components that are involved in the estimation of the GV.

Example 15

Methods 12 patients (mean age 35.7 std 14.4) with PVH were studied with the HTR. Bed side examination, electronystagmography (ENG) with rotatory and caloric test, audiological testing and MRI scan assessment were performed in all the patients. PVH was defined in the ENG by the bithermal test based on the Jongkee's formula [9]. Informed consent was obtained from the patients, according to the ethical standards of the Helsinki Declaration (1975 revised 1983).

FIG. 23 shows the gender, age and diagnosis of the patients who have PVH discriminating those who had CD (group A) as a main disabling symptom. A patient is considered with CD when he has daily imbalance and an increase of dizziness symptoms in open spaces. Bed side examination shows catch up saccades in the head thrust test. All of the Patients with these characteristics of CD are described as "uncompensated". Those patients without CD (group B) are considered as "compensated". The HTR test was also performed in volunteers (N=23, age 26±5.6) without any reports of vestibular symptoms as a control group (group C).

Example 16

Experimental Setup and HTR Description

As described in the previously disclosed experimentation, subjects stand on a firm horizontal surface wearing virtual reality goggles (Z800 3Dvisor, eMagin) and a light isolator to ensure that no external visual references are available. Subjects are only exposed to the stimulus displayed on the goggles. A head tracking device (InertiaCube2+, Intersense) is attached to the goggles to keep record of the head angle with respect to the GV. The stimulus displayed on the goggles is a white bar presented over a black background as shown on FIG. 19a.

Figure 19:
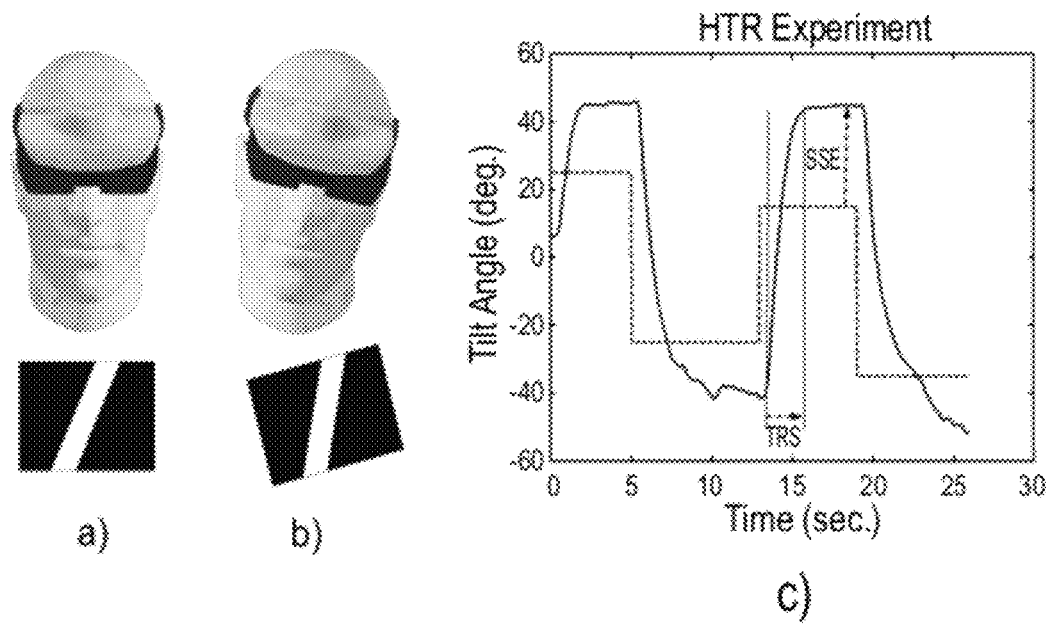
FIG. 19 demonstrates, in accordance with an embodiment of the invention, a) Subject with his head in upright position and the image seen on the goggles, presenting the white bar over black background. b) Subject with his head tilted a small number of degrees. The white bar tilt is closer to the GV but has not yet reached it. Images are as seen by the subject. c) Typical HTR test data with the reference signal data (dashed line) and a typical subject's response data (solid line). The reference signal designed indicates the angle of the white bar with respect to the goggles vertical axis. The subject's response indicates its head roll angle trying to match the angle of the bar. Two main characteristics of the transient response are shown: the steady state error (SSE) between the angles achieved by the subject and the reference signal and the time it takes for the subject to get for the first time close enough to its final position, called Rise Time.

Subjects are presented with the stimulus on the virtual reality goggles (Head Mounted Display, HMD) and they are asked to tilt their heads to align the bar with the GV (FIG. 19 a,b). All subjects were instructed to start moving the bar as soon as a new image appears on the goggles. When the exercise starts, the image of the bar is presented with a certain inclination for a specific amount of time, and then a new bar with a different orientation appears on the screen. When the subject perceives that the white bar is aligned with the GV they should remain in that position until a new bar appears on the display. When the screen goes black, the trial is over. This process is repeated 5 times with the same parameters, taking the whole test approximately 5 minutes. Head inclination is recorded at 50 Hz.

Example 17

Measurement of the Responses

In this particular set of experiments, the parameters studied were: 1—rise time (TRS): time (in seconds) that a subject takes to move its head from 5% to 95% of the bar step, and 2—steady state error (SSE): the angle difference between the reference signal and the head tilt angle as a percentage of the step.

TRS and SSE parameters are shown in FIG. 19c), which are typically used to characterize a dynamic system step response. The format of the HTR test means that five sets of two parameters each are obtained per step and per subject. Mean value over trials is calculated for each of the two parameters to generate two unique vectors of parameters for each individual per step. For the twenty-three mean values that characterize the population of normal subjects per parameter, mean and standard deviation are found. The parameters obtained for group C were checked against a normal distribution using the Kolmogorov-Smirnov (KS) test (alpha=5%), finding its mean and confidence intervals.

The set of vectors obtained for the whole population of normal subjects were analyzed to find relationships and cues that may characterize a normal subject response to this test.

Example 18

Statistical Analysis

Normal distribution was not rejected using KS test for the normal population (group C). For SSE p=0.53 and for TRS p=0.88. The three Sigma ellipse was calculated for this group. Any subject response falling outside of this ellipse implies that the subject has at most 1% chance of belonging to the same population. To determine the discriminative characteristics of each parameter alone, ROC curves were used. These curves are plotted using the specificity and sensitivity of the sample and determining the cut-off point by maximizing these values. A common value to compare between classifiers is to use the area under the ROC curves (AUC), which is a value between 0.5 (random guessing) and 1 (perfect classifier). All data were analyzed using Matlab.

Example 19

Results

FIG. 23 shows eight patients of group A (PVH with CD) and four patients of group B (PVH without CD). Related with the additional testing, all patients except number four had ipsilateral sensoryneural hearing loss.

Figure 20:
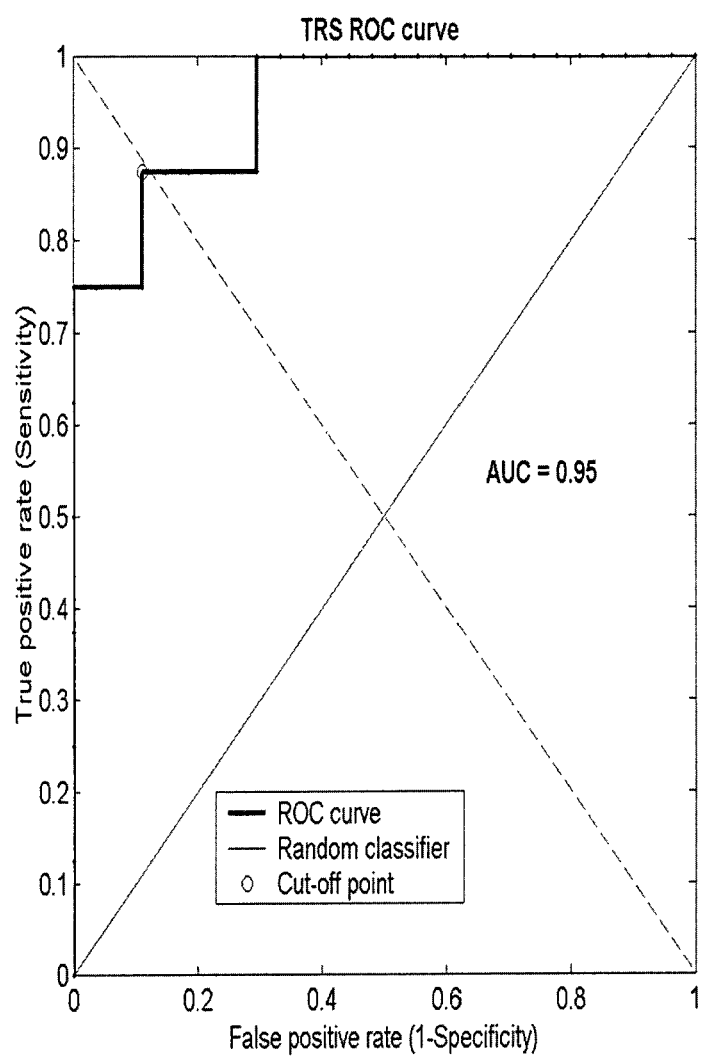
FIG. 20 demonstrates, in accordance with an embodiment of the invention, ROC curves of specificity and sensitivity for TRS.
Figure 21:
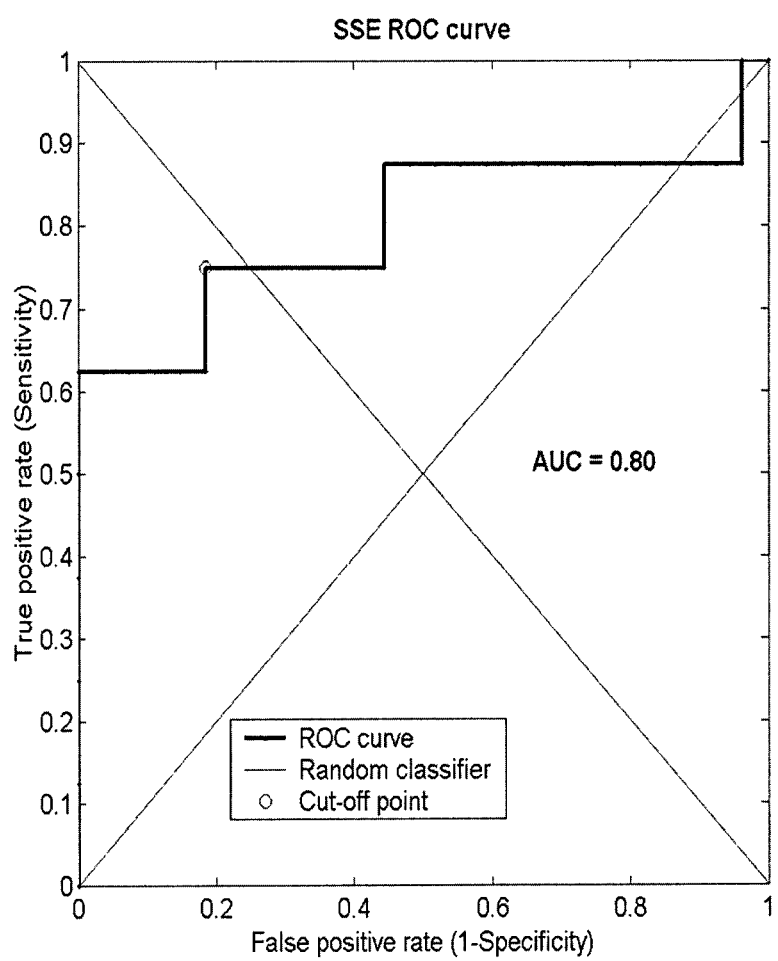
FIG. 21 demonstrates, in accordance with an embodiment of the invention, ROC curves of specificity and sensitivity for SSE.

Group A patients (patients 1-8) had larger rise time (TRS) and steady state error (SSE) compared to group B (patients 9-12) and group C. ROC curves [10] for TRS and SSE parameters were applied to compare groups in order to analyze the specificity (probability that test is negative on healthy subject) and sensitivity (probability that test is positive on a subject with CD) of these parameters as a potential "marker" of CD. SSE shows 81.5% of specificity and 75% of sensitivity while TRS shows 88.9% and 87.5% respectively (FIGS. 20 and 21).

Figure 22:
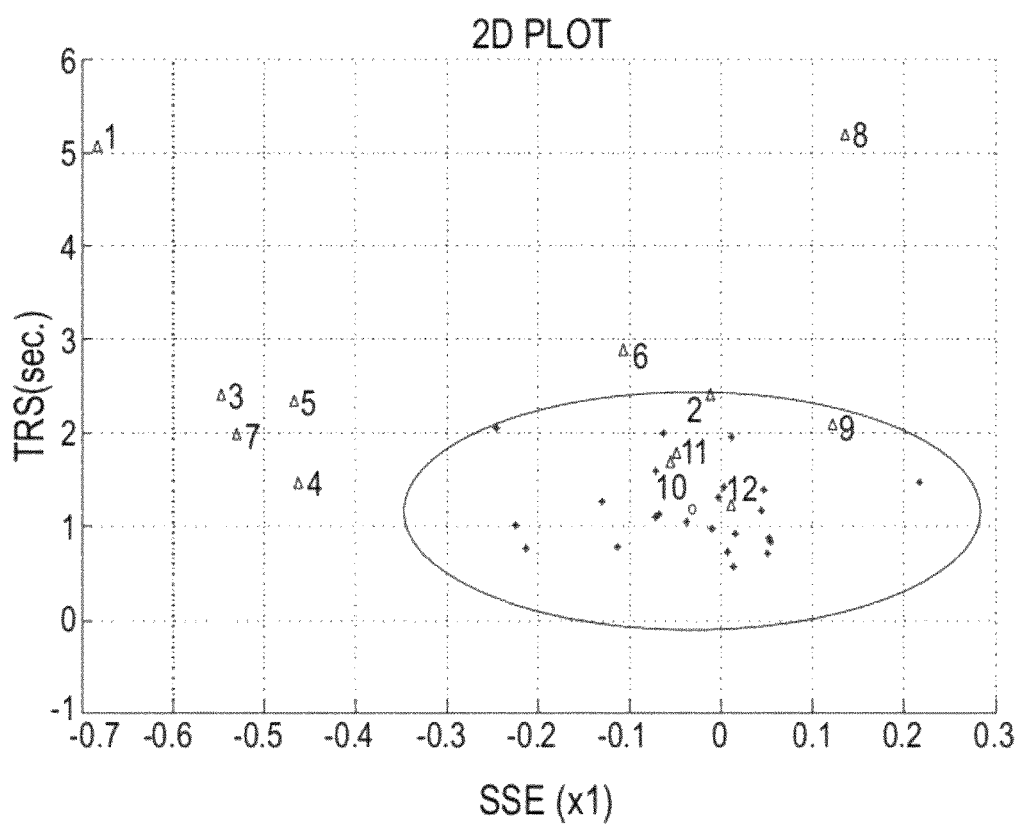
FIG. 22 demonstrates, in accordance with an embodiment of the invention, a two dimensional plot showing TRS vs SSE for all groups. A 3-sigma ellipse is also shown specifying 99% confidence range for the distribution of normal subjects (Labeled as black *—group C). Triangular markers for subjects with PVH are numbered. Patients 1 to 8 have CD (Group A). Patients 9 to 12 belong to group B.

Although in an isolated analysis of each of these parameters, TRS is a better marker than SSE to establish the visual vertical gravitational perception skill, a better discrimination for group A patients (control plus PVH without CD) is achieved by a 2 dimensional analysis (SSE versus TRS). FIG. 22 shows a 2 dimensional plot using SSE and TRS mean values for all subjects in all groups. The 3 Sigma ellipse calculated is also drawn.

Example 20

Discussion

The most remarkable findings of this study are a delay in the estimation of GV (TRS) and wrong estimation in the angle of the visual vertical (SSE), facts which are very significant in patients who have a non-compensated PVH with CD (group A) as the main symptom. Given the design characteristics of the test, the delay in the GV estimation (TRS) could be explained by the absence of suitable information from the vestibular receptors. While not wishing to be bound by any one particular theory, the visual vertical estimation could be achieved from other sources of information such as a somatosensory input, or perhaps the subject is using the "internal model" of the GV. This could explain the increase in the time needed to estimate the GV. Some central nervous system diseases with adequate vestibular end organs information have alterations in the subjective visual vertical [11,12]. This could be explained by an altered "internal model" of the GV. While not wishing to be bound by any one particular theory, these findings would mean that this internal model is essential and is the main source for the GV altered behavior in patients with PVH.

In relation with the somatosensory input as an alternative source of information for the GV, some reports claim the limited influence of the proprioceptive neck information for the visual vertical perception [13]. Besides, the kind of substitutive source of information (Internal model or proprioceptive information) required by patients with a non-compensated PVH (with CD), implies a longer GV estimation time and greater steady state angle error. These altered values of TRS and SSE represent the uncertainty of the control system for the GV estimation and the head tilt position, which may be clinically expressed as CD. ROC curves showed that TRS has high specificity and sensitivity for the different behavior between patients with PVH and CD, and the rest of the population. Based upon the cumulative experimentation reported herein, it seems likely that TRS values could be a quantitative marker of vestibular compensation after a lesion of the peripheral vestibular end organs.

Example 21

Influences of Altered Neck Muscles and Low Extremities Information on Head Tilt Response Test As previously disclosed herein, perception of earth (gravitational)-vertical is determined by the correct central fusion of information arriving from the retina, vestibular end organs and different somatosensory sensors. Different conditions may lead to an altered perception and estimation of verticality, although there are some controversies about its interpretation and correlation with a specific dysfunction. Previous communications have shown changes in the perception of gravitational vertical when vibration is applied to the neck muscles.

As previously described herein, a dynamic test can be used to evaluate a subject's perception of verticality, called the Head Tilt Response (HTR) (J Vestib Res. 2010; 20 (5):381-9). 5 parameters are evaluated and characterized to analyze the Head Tilt Response: 1) Steady state error: Steady state angle error between the bar position and head position. 2) Rise time: Time (in seconds) it takes for the subject to move its head from 5% to 95% of the bar step. 3)

Overshoot: Some subjects may overreact to a bar angle change and tilt their heads a larger angle than necessary before coming down to the right value. The value of this maximum head tilt as a percentage of the right angle needed is usually called overshoot. 4) Settling time: Time (in seconds) to reach its steady state angle within 2%. 5) Delay time: Time it takes for the subject to react to a step in the bar angle.

The influence of a disturbance in the information from 2 different somatosensory cues, in perception of verticality through the HTR can be studied: muscular neck afference and an altered base of support. Testing can be performed under 4 different conditions, while the subject is in a standing position with no external perturbation, with foam as the base of support, applying vibration in the subjects' necks, and with the last two conditions applied together. In one version of the experiment, 2 different populations are studied and compared, a normal control group and a group of patients with unilateral peripheral vestibular loss, clinically compensated. Differences in the HTR responses can be detected according to the condition analyzed. Also, differences between normal subjects and those with a compensated unilateral peripheral vestibular deficit in HTR response can be determined.

Example 22

Computing Device

Figure 17:
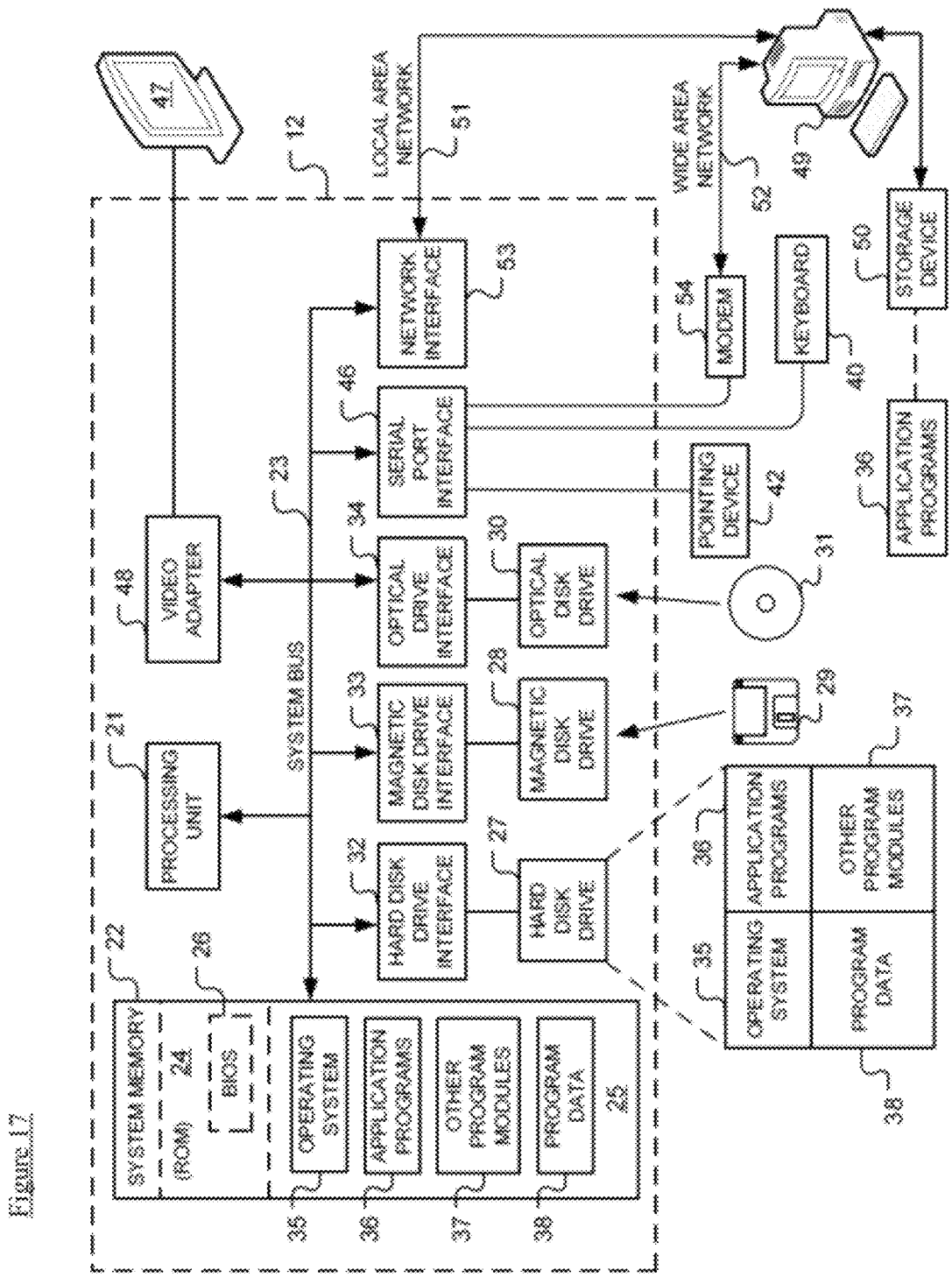
FIG. 17 demonstrates, in accordance with an embodiment of the invention, a diagram of a hardware environment and an operating environment in which the components and the computing devices of FIGS. 13-16 may be implemented.

FIG. 17 is a diagram of hardware and an operating environment in conjunction with which implementations of the systems (100, 200, 300 and 400), computing devices (150, 240, 330 and 450), and components (120, 130, 140, 220, 230, 320, 420, 430 and 440) may be practiced. The description of FIG. 17 is intended to provide a brief, general description of suitable computer hardware and a suitable computing environment in which implementations may be practiced. Although not required, implementations are described in the general context of computer-executable instructions, such as program modules, being executed by a computer, such as a personal computer. Generally, program modules include routines, programs, objects, components, data structures, etc., that perform particular tasks or implement particular abstract data types.

Moreover, those skilled in the art will appreciate that implementations may be practiced with other computer system configurations, including hand-held devices, multi-processor systems, microprocessor-based or programmable consumer electronics, network PCs, minicomputers, mainframe computers, and the like. Implementations may also be practiced in distributed computing environments where tasks are performed by remote processing devices that are linked through a communications network. In a distributed computing environment, program modules may be located in both local and remote memory storage devices.

One of skill in the art would readily appreciate the numerous ways in which the inventive method could be implemented through the use of cloud computing, whereby shared resources, software, and information of the presently disclosed systems and methods are provided to computers and other devices as a utility over a network, including the internet.

The exemplary hardware and operating environment of FIG. 17 includes a general-purpose computing device in the form of a computing device 12. The computing devices 150, 240, 330 and 450 may each be implemented using one or more computing devices like the computing device 12.

The computing device 12 includes a system memory 22, the processing unit 21, and a system bus 23 that operatively couples various system components, including the system memory 22, to the processing unit 21. There may be only one or there may be more than one processing unit 21, such that the processor of computing device 12 includes a single central-processing unit ("CPU"), or a plurality of processing units, commonly referred to as a parallel processing environment. When multiple processing units are used, the processing units may be heterogeneous. By way of a non-limiting example, such a heterogeneous processing environment may include a conventional CPU, a conventional graphics processing unit ("GPU"), a floating-point unit ("FPU"), combinations thereof, and the like. The computing device 12 may be a conventional computer, a distributed computer, or any other type of computer.

The system bus 23 may be any of several types of bus structures including a memory bus or memory controller, a peripheral bus, and a local bus using any of a variety of bus architectures. The system memory 22 may also be referred to as simply the memory, and includes read only memory (ROM) 24 and random access memory (RAM) 25. A basic input/output system (BIOS) 26, containing the basic routines that help to transfer information between elements within the computing device 12, such as during start-up, is stored in ROM 24. The computing device 12 further includes a hard disk drive 27 for reading from and writing to a hard disk, not shown, a magnetic disk drive 28 for reading from or writing to a removable magnetic disk 29, and an optical disk drive 30 for reading from or writing to a removable optical disk 31 such as a CD ROM, DVD, or other optical media.

The hard disk drive 27, magnetic disk drive 28, and optical disk drive 30 are connected to the system bus 23 by a hard disk drive interface 32, a magnetic disk drive interface 33, and an optical disk drive interface 34, respectively. The drives and their associated computer-readable media provide nonvolatile storage of computer-readable instructions, data structures, program modules, and other data for the computing device 12. It should be appreciated by those skilled in the art that any type of computer-readable media which can store data that is accessible by a computer, such as magnetic cassettes, flash memory cards, solid state memory devices ("SSD"), USB drives, digital video disks, Bernoulli cartridges, random access memories (RAMs), read only memories (ROMs), and the like, may be used in the exemplary operating environment. As is apparent to those of ordinary skill in the art, the hard disk drive 27 and other forms of computer-readable media (e.g., the removable magnetic disk 29, the removable optical disk 31, flash memory cards, SSD, USB drives, and the like) accessible by the processing unit 21 may be considered components of the system memory 22.

A number of program modules may be stored on the hard disk drive 27, magnetic disk 29, optical disk 31, ROM 24, or RAM 25, including an operating system 35, one or more application programs 36, other program modules 37, and program data 38. A user may enter commands and information into the computing device 12 through input devices such as a keyboard 40 and pointing device 42. Other input devices (not shown) may include a microphone, joystick, game pad, satellite dish, scanner, touch sensitive devices (e.g., a stylus or touch pad), video camera, depth camera, or the like. These and other input devices are often connected to the processing unit 21 through a serial port interface 46 that is coupled to the system bus 23, but may be connected by other interfaces, such as a parallel port, game port, a universal serial 5 bus (USB), or a wireless interface (e.g., a Bluetooth interface). A monitor 47 or other type of display device is also connected to the system bus 23 via an interface, such as a video adapter 48. In addition to the monitor, computers typically include other peripheral output devices (not shown), such as speakers, printers, and haptic devices that provide tactile and/or other types physical feedback (e.g., a force feedback game controller).

The computing device 12 may operate in a networked environment using logical connections to one or more remote computers, such as remote computer 49. These logical connections are achieved by a communication device coupled to or a part of the computing device 12 (as the local computer). Implementations are not limited to a particular type of communications device.

The remote computer 49 may be another computer, a server, a router, a network PC, a client, a memory storage device, a peer device or other common network node, and typically includes many or all of the elements described above relative to the computing device 12. The remote computer 49 may be connected to a memory storage device 50. The logical connections depicted in FIG. 17 include a local-area network (LAN) 51 and a wide-area network (WAN) 52. Such networking environments are commonplace in offices, enterprise-wide computer networks, intranets and the Internet.

Those of ordinary skill in the art will appreciate that a LAN may be connected to a WAN via a modem using a carrier signal over a telephone network, cable network, cellular network, or power lines. Such a modem may be connected to the computing device 12 by a network interface (e.g., a serial or other type of port). Further, many laptop computers may connect to a network via a cellular data modem.

When used in a LAN-networking environment, the computing device 12 is connected to the local area network 51 through a network interface or adapter 53, which is one type of communications device. When used in a WAN networking environment, the computing device 12 typically includes a modem 54, a type of communications device, or any other type of communications device for establishing communications over the wide area network 52, such as the Internet. The modem 54, which may be internal or external, is connected to the system bus 23 via the serial port interface 46. In a networked environment, program modules depicted relative to the personal computing device 12, or portions thereof, may be stored in the remote computer 49 and/or the remote memory storage device 50. It is appreciated that the network connections shown are exemplary and other means of and communications devices for establishing a communications link between the computers may be used.

The computing device 12 and related components have been presented herein by way of particular example and also by abstraction in order to facilitate a high-level view of the concepts disclosed. The actual technical design and implementation may vary based on particular implementation while maintaining the overall nature of the concepts disclosed.

The foregoing described embodiments depict different components contained within, or connected with, different other components. It is to be understood that such depicted architectures are merely exemplary, and that in fact many other architectures can be implemented which achieve the same functionality. In a conceptual sense, any arrangement of components to achieve the same functionality is effectively "associated" such that the desired functionality is achieved. Likewise, any two components so associated can also be viewed as being "operably connected", or "operably coupled", to each other to achieve the desired functionality.

While particular embodiments of the present invention have been shown and described, it will be obvious to those skilled in the art that, based upon the teachings herein, changes and modifications may be made without departing from this invention and its broader aspects and, therefore, the appended claims are to encompass within their scope all such changes and modifications as are within the true spirit and scope of this invention. Furthermore, it is to be understood that the invention is solely defined by the appended claims. It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.).

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to inventions containing only one such recitation, even when the same claim includes the introductory phrases "one or more" or "at least one" and indefinite articles such as "a" or "an" (e.g., "a" and/or "an" should typically be interpreted to mean "at least one" or "one or more"); the same holds true for the use of definite articles used to introduce claim recitations. In addition, even if a specific number of an introduced claim recitation is explicitly recited, those skilled in the art will recognize that such recitation should typically be interpreted to mean at least the recited number (e.g., the bare recitation of "two recitations," without other modifiers, typically means at least two recitations, or two or more recitations).

Accordingly, the invention is not limited except as by the appended claims.

REFERENCES

[1] Aubert, H. Eine scheinbare bedeutende drehung von objecten beineigung des kopfes nach rechts oder links. Virchows Arch, 20, 381-393(1861)

[2] Böhmer, Andreas; Mast, Fred. Assessing Otolith Function by the Subjective Visual Vertical. Annals of the New York Academy of Sciences: 871, 1999, pp 221-231

[3] Bohmer, Andreas. The Subjective Visual Vertical as a Clinical Parameter for Acute and Chronic Vestibular (Otolith) Disorders. Acta Otolaryngol (Stockh) 1999; 119: 126-127

[4] Bronstein A M. The interaction of otolith and proprioceptive information in the perception of verticality. The effects of labyrinthine and CNS disease. Ann. NY Acad. Sci. 1999 May 28; 871:324-33

[5] Clarke, A. H. Schoenfeld, U. Hamann C. and Scherer H. Measuring Unilateral Otolith Function Via the Otolith-ocular Response and the Subjective Visual Vertical. Acta Otolaryngol 2001; Suppl 545: 84-87

[6] Clarke, A. H. and Engelhorn, A. Unilateral testing of utricular function. Exp. Brain Res. 121 (1998). 457-464.

[7] Clarke, A. H. The many facets of the otolith—a review. J Vestib Res 11(3-5), 314 (2002).

[8] Daddaoua, Nabil. Dicke, Peter W. Their, Peter. The subjective visual vertical in a nonhuman primate. Journal of Vision (2008)8(3):19, 1-8

[9] Dorf, Richard. and Bishop, Robert. Modern Control Systems, 11th edition, pp 1018, Prentice Hall, 2008.

[10] Fischer, M. H. Z. Messende Untersuchungen über die Gegenrollungder Augen and die Lokalisation der scheinbaren Vertikalen. v. Graefe's Arch. Ophthal. 118 (1927). 633-680.

[11] Karlberg, Mikael. Aw, Swee T. Halmagyi, G. Michael. Black, RossA. Vibration-Induced Shift of the Subjective Horizontal. A sign of unilateral vestibular deficit. Arch. Otolaryngol Head Neck Surg. 2002; 128:21-27.

[12] Kobayashia, Hironari. Hayashia, Yujiro. Higashinoa, Kazutaka. Saitob, Akira. Kunihiroa, Takanobu. Kanzakia, Jin and Goto, Fumiyuki. Dynamic and static subjective visual vertical with aging. Auris NasusLarynx Volume 29, Issue 4, 1 Oct. 2002, Pages 325-328

[13] Mars, Franck; Vercher, Jean-Louis and Blouin, Jean. Perception of the vertical with a head-mounted visual frame during head tilt, Ergonomics (2004), 47:10, 1116-1130

[14] Nechel, Ch. Van. Toupet, M. Bodsona, I. The Subjective Visual Vertical. Otolith Functions and Disorders. Adv Otorhinolaryngol. Basel, Karger, 2001, vol 58, pp 77-87

[15] Ogata, Katsuhiko. Modern Control Engineering (4th Edition). Prentice Hall 2001.

[16] Sachs, L. Applied Statistics: A Handbook of Techniques, 2nd, edition Springer 1984.

[17] Schöne, H. Über den Einfluβ der Schwerkraft auf die Augenrollungund die Wahrnehmung der Lage im Raum. Z. vergl. Physiol. 46 (1962). 57-87.

[18] Strupp, M; Glasauer, S; Schneider, E; Eggert, T; Glaser, M; Jahn, K; Brandt, T. Anterior canal failure: ocular torsion withoutperceptual tilt due to preserved otolith function. Journal of Neurology Neurosurgery and Psychiatry 2003; 74:1336-1338

[19] Strupp, Michael. Arbusow, Victor. Dieterich, Marianne. Sautier, Wolfram and Brandt, Thomas. Perceptual and oculomotor effects of neckmuscle vibration in vestibular neuritis. Brain (1998), 121, 677-685

[20] Tarnutzer, Alexander Andrea. Bockisch, Christopher J. Straumann, Dominik and Olasagasti, Itsaso. Gravity-dependence of subjective visual vertical variability. J Neurophysiol, July 2009.

[21] Tribukait, A. Bergenius, J. and Brantberg, K. Subjective Visual Horizontal During Follow-up After Unilateral Vestibular Deafferentation with Gentamicin. Acta Otolaryngol (Stockh) 1998; 118:479-487

[22] Wetzig, J. Hofstetter-Degen, K. Maurer, J. and Baumgarten, R. von. Clinical verification of a unilateral otolith test. Acta Astronautica27 (1992). 19-24.

[23] Wuyts, F. L. Hoppenbrouwers, M. Pauwels, G. and Heyning, P. vande. Unilateral otolith function testing—is the utricular functionadditive? Abstract Bárány Meeting 2002. J. Vestib. Res. 11 (2002). 304.

SUPPLEMENTAL REFERENCES

Böhmer, Andreas; Mast, Fred. Assessing Otolith Function by the Subjective Visual Vertical. Annals of the New York Academy of Sciences: 871, 1999, pp 221-231

Aubert, H. Eine scheinbare bedeutende drehung von objecten beineigung des kopfes nach rechts oder links. Virchows Arch, 20, 381-393 (1861)

Fischer, M. H. Z. Messende Untersuchungen über die Gegenrollung der Augen und die Lokalisation der scheinbaren Vertikalen. v. Graefe's Arch. Ophthal. 118 (1927). 633-680.

Schön, H. Über Uden Einfluβ der Schwerkraft auf die Augenrollung und die Wahrnehmung der Lage im Raum. Z. vergl. Physiol. 46 (1962). 57-87.

Kobayashia, Hironari. Hayashia, Yujiro. Higashinoa, Kazutaka. Saitob, Akira. Kunihiroa, Takanobu. Kanzakia, Jin and Goto, Fumiyuki. Dynamic and static subjective visual vertical with aging. Auris Nasus Larynx Volume 29, Issue 4, 1 Oct. 2002, Pages 325-328

Wetzig, J. Hofstetter-Degen, K. Maurer, J. and Baumgarten, R. von. Clinical verification of a unilateral otolith test. Acta Astronautica 27 (1992). 19-24.

Clarke, A. H. and Engelhorn, A. Unilateral testing of utricular function. Exp. Brain Res. 121 (1998). 457-464.

Wuyts, F. L. Hoppenbrouwers, M. Pauwels, G. and Heyning, P. van de. Unilateral otolith function testing—is the utricular function additive? Abstract Bárány Meeting 2002. J. Vestib. Res. 11 (2002). 304.

Bohmer, Andreas. The Subjective Visual Vertical as a Clinical Parameter for Acute and Chronic Vestibular (Otolith) Disorders. Acta Otolaryngol (Stockh) 1999; 119: 126-127

Daddaoua, Nabil. Dicke, Peter W. Their, Peter. The subjective visual vertical in a nonhuman primate. Journal of Vision (2008)8(3):19, 1-8

Bronstein A M. The interaction of otolith and proprioceptive information in the perception of verticality. The effects of labyrinthine and CNS disease. Ann. NY Acad. Sci. 1999 May 28; 871:324-33

Clarke, AH. The many facets of the otolith—a review. J Vestib Res 11(3-5), 314 (2002).

Strupp, M; Glasauer, S; Schneider, E; Eggert, T; Glaser, M; Jahn, K; Brandt, T. Anterior canal failure: ocular torsion without perceptual tilt due to preserved otolith function. Journal of Neurology Neurosurgery and Psychiatry 2003; 74:1336-1338

Mars, Franck; Vercher, Jean-Louis and Blouin, Jean. Perception of the vertical with a head-mounted visual frame during head tilt, Ergonomics (2004), 47:10, 1116-1130

Clarke, A. H. Schoènfeld, U. Hamann C. and Scherer H. Measuring Unilateral Otolith Function Via the Otolithocular Response and the Subjective Visual Vertical. Acta Otolaryngol 2001; Suppl 545: 84-87

Nechel, Ch. Van. Toupet, M. Bodsona, I. The Subjective Visual Vertical. Otolith Functions and Disorders. Adv Otorhinolaryngol. Basel, Karger, 2001, vol 58, pp 77-87

Tarnutzer, Alexander Andrea. Bockisch, Christopher J. Straumann, Dominik and Olasagasti, Itsaso. Gravity-dependence of subjective visual vertical variability. J Neurophysiol, July 2009.

Dario Geisinger, Enrique Ferreira, Alejo Suarez and Hamlet Suarez. Head Tilt Response: A complementary test to the Subjective Visual Vertical. Journal of Vestibular Research (accepted for publication). L. Ljung, "System Identification: Theory for the User", $2^{nd}$ edition, Prentice Hall, 1999.

REFERENCES FOR ADDITIONAL EXPERIMENTS

[1] Girshick A R, Landy M S, Simoncelli E P. Cardinal rules: visual orientation perception reflects knowledge of environmental statistics. Nat Neurosci. 2011 Jun. 5; 14(7): 926-32.

[2] Liao K, Walker M F, Joshi A, Reschke M, Strupp M, Leigh R J. The human vertical translational vestibulo-ocular reflex. Normal and abnormal responses Ann N Y Acad Sci. 2009 May; 1164: 68-75.

[3] Grabherr L, Cuffel C, Guyot J P, Mast F W. Mental transformation abilities in patients with unilateral and bilateral vestibular loss. Exp Brain Res. 2011 March; 209(2):205-14.

[4] Goto F, Ban Y, Tsutumi T. Acute audiovestibular deficit with complete ocular tilt reaction and absent VEMPs. Eur Arch Otorhinolaryngol. 2011 July; 268(7):1093-6.

[5] A. Bohmer and F. Mast, Assessing Otolith Function by the Subjective Visual Vertical, Annals of the New York Academy of Sciences 871 (1999), 221-231.

[6] A. M. Bronstein, The interaction of otolith and proprioceptive information in the perception of verticality, The effects of labyrinthine and CNS disease, Ann NY Acad Sci 871 (28 May 1999), 324-333.

[7] Geisinger D, Ferreira E, Suarez A, Suarez H. Head tilt response: A complementary test to the Subjective Visual Vertical.) Vestib Res. 2010; 20(5):381-9.

[8] Nogueira S, Ferreira E, Geisinger D, San Román C, Suarez H. Model of postural control system applied in Parkinson's disease patients. Conf Proc IEEE Eng Med Biol Soc. 2010; 2010:5452-5.

[9] Formby C, Carter R L, Hansen C A, Kuntz, L A. Measurement, analysis and modelling of the caloric response. 1. A descriptive mathematical model of the caloric response over time. Acta Otolaryngol (Stock) 1992:Suppl 498, 4-18

[10] Bradley A. The use of the area under the ROC curve in the evaluation of machine learning algorithms. Pattern Recognition. 1997; 30(7):1145-1159.

[11] Murdin L, Bronstein A M Head deviation in progressive supranuclear palsy: enhanced vestibulo-collic reflex or loss of resetting head movements. J. Neurol. 2009 July; 256(7):1143-5.

[12] Nys G M, Santens P, Vingerhoets G (CNS y VV). Horizontal and vertical attentional orienting in Parkinson's disease. Brain Cogn. 2010 December; 74(3):179-85.

[13] Funabashi M, Silva N N, Watanabe L M, Santos-Pontelli T E, Colafêmina J F, Carneiro A A, Takayanagui O M. The use of a neck brace does not influence visual vertical perception. Arq Neuropsiquiatr. 2011 June; 69(3): 509-12.

What is claimed is:

1. A system for determining a subject's perception of the gravitational vertical, the system comprising:
virtual reality goggles configured to display an image at an angle greater than zero degrees to the gravitational vertical;
a head tracking device configured to track the motion and the position of the subject's head in response to the image;
a data storage comprising a head motion and position capturing and analyzing application; and
a processor operatively coupled to: the virtual reality goggles, the head tracking device, and the data storage comprising a head motion and position capturing and analyzing application, wherein, upon execution, the virtual reality goggles display the image at an angle of greater than zero degrees to the gravitational vertical, the head tracking device tracks the motion and position of the subject's head in response to the image, and the head motion and position capturing and analyzing application:
(a) determines the subject's head motion and position in response to the image, and
(b) determines the subject's perception of the gravitational vertical, based upon one or more parameters determined based on the position of subject's head relative to an angle of the image and selected from the group consisting of: steady state error (SSE), delay time (TDT), rise time (TRS), settling time (TST), overshoot (OSP), integral time square absolute error (IT2AE) and combinations thereof.

2. The system of claim 1, further comprising:
an eye motion tracking device configured to track the motion of the subject's eyes; and
an eye motion tracking application, wherein the processor is operatively coupled to the eye motion tracking device, and wherein upon execution, the eye motion tracking device tracks the motion of the subject's eyes.

3. A computer readable medium having computer-executable components that, when executed by a computing device coupled to: virtual reality goggles capable of displaying an image at an angle of greater than zero degrees to the gravitational vertical, and one or more electronic device configured to measure and record the motion and position of a subject's head in response to the image, cause: the virtual reality goggles to display an image at an angle greater than zero degrees to the gravitational vertical; the head tracking device to measure and record the motion and position of the subject's head in response to the image; and the computing device to (a) measure parameters determined based on the position of the subject's head relative to an angle of the image and selected from the group consisting of: steady state error (SSE), delay time (TDT), rise time (TRS), settling time (TST), overshoot (OSP), integral time square absolute error (IT2AE) and combinations thereof, and (b) determine the subject's perception of gravitational vertical based upon the measured parameters.

* * * * *